(12) United States Patent
Hashash et al.

(10) Patent No.: US 8,841,340 B2
(45) Date of Patent: Sep. 23, 2014

(54) SOLID FORMS OF AN ANTIVIRAL COMPOUND

(71) Applicant: Gilead Sciences, Inc., Foster City, CA (US)

(72) Inventors: Ahmad Hashash, Shrewsbury, MA (US); Scott Wolckenhauer, Redwood City, CA (US); Bing Shi, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/800,991

(22) Filed: Mar. 13, 2013

(65) Prior Publication Data

US 2014/0051749 A1    Feb. 20, 2014

Related U.S. Application Data

(60) Provisional application No. 61/684,297, filed on Aug. 17, 2012.

(51) Int. Cl.
  *A01N 43/06* (2006.01)
  *A61K 31/38* (2006.01)
  *C07D 409/00* (2006.01)

(52) U.S. Cl.
  USPC ............................................ 514/444; 549/60

(58) Field of Classification Search
  USPC ............................................ 514/444; 549/60
  See application file for complete search history.

(56) References Cited

U.S. PATENT DOCUMENTS

| | | | |
|---|---|---|---|
| 5,861,421 | A | 1/1999 | Christensen, IV et al. |
| 6,881,741 | B2 | 4/2005 | Chan Chun Kong et al. |
| 6,887,877 | B2 | 5/2005 | Chan Chun Kong et al. |
| 7,402,608 | B2 | 7/2008 | Chan Chun Kong et al. |
| 7,521,473 | B2 | 4/2009 | Lee et al. |
| 7,569,600 | B2 | 8/2009 | Denis et al. |
| 2002/0002199 | A1 | 1/2002 | Jeppesen et al. |
| 2003/0229053 | A1 | 12/2003 | Chan Chun Kong et al. |
| 2004/0116509 | A1 | 6/2004 | Chan Chun Kong et al. |
| 2005/0052161 | A1 | 3/2005 | Watkins |
| 2005/0119332 | A1 | 6/2005 | Jeppesen et al. |
| 2006/0142347 | A1 | 6/2006 | Chan Chun Kong et al. |
| 2006/0276533 | A1 | 12/2006 | Denis et al. |
| 2007/0099929 | A1 | 5/2007 | Thede et al. |
| 2008/0299080 | A1 | 12/2008 | Chan Chun Kong et al. |
| 2009/0274655 | A1 | 11/2009 | Grimes et al. |
| 2011/0020278 | A1 | 1/2011 | Canales et al. |
| 2011/0178058 | A1 | 7/2011 | Canales et al. |
| 2011/0178129 | A1 | 7/2011 | Canales et al. |
| 2013/0052161 | A1 | 2/2013 | Watkins et al. |

FOREIGN PATENT DOCUMENTS

| | | |
|---|---|---|
| WO | 02/100846 A1 | 12/2002 |
| WO | 02/100851 A2 | 12/2002 |
| WO | 2004/052885 | 6/2004 |
| WO | 2005/095386 A1 | 10/2005 |
| WO | 2006/072347 A2 | 7/2006 |
| WO | 2006/072348 | 7/2006 |
| WO | 2007/093365 A2 | 8/2007 |
| WO | 2008/058393 A1 | 5/2008 |
| WO | 2010/065668 | 6/2010 |
| WO | 2011/011303 | 1/2011 |
| WO | 2011/031669 | 3/2011 |
| WO | 2011/068715 | 6/2011 |
| WO | 2011/088345 A1 | 7/2011 |
| WO | 2012/006055 | 1/2012 |
| WO | 2012/087596 A1 | 6/2012 |

OTHER PUBLICATIONS

U.S. Appl. No. 13/801,011, filed Mar. 13, 2013, Watkins et al.
U.S. Appl. No. 13/801,039, filed Mar. 13, 2013, Evans et al.
Boyer, N, et al. (2000) "Pathogenesis, diagnosis and management of hepatitis C," *Journal of Hepatology* 32 (suppl 1):98-112.
Calisher, C. et al. (1989) "Antigenic Relationships between *Flaviviruses* as Determined by Cross-neutralization Tests with Polyclonal Antisera," *J.gen. Virol.* 70:37-43.
Di Bisceglie, a. et al. (1999) "Some 1.8 percent of the U.S. adult population are infected with the hepatitis C virus, most without knowing it" *Scientific American* October pp. 80-85.
Domingo, E. et al. (1985) "The quasispecies (extremely heterogeneous) nature of viral RNA genome populations: biological relevance—a review" *Gene* 40:1-8.
Dymock, B. et al. (2000) "Novel approaches to the treatment of hepatitis C virus infection," *Antiviral Chemistry & Chemotherapy* 11(2):79-96.

(Continued)

*Primary Examiner* — Kendra D Carter
(74) *Attorney, Agent, or Firm* — Kilpatrick, Townsend & Stockton LLP

(57) ABSTRACT

Crystalline solid forms and the amorphous form of the anti-HCV compound 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I) were prepared and characterized in the solid state:

Compound I

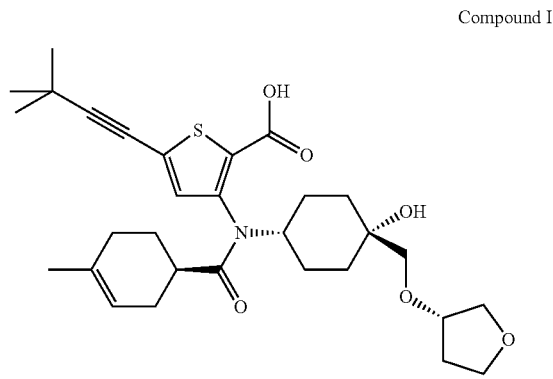

Also provided are processes of manufacture and methods of using the crystalline forms.

26 Claims, 28 Drawing Sheets

(56) References Cited

OTHER PUBLICATIONS

Fukumoto, T. et al. (1996) "Viral Dynamics of Hepatitis C Early After Orthotopic Liver Transplantation: Evidence for Rapid Turnover of Serum Virions," *Hepatology* 24:1351-1354.

Gordon, C. et al. (2005) "Control of Hepatitis C: A Medicinal Chemistry Perspective," *Journal of Medicinal Chemistry* 48(1):1-20.

Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.

Maradpour, D. et al. (2007) "Replication of Hepatitis C Virus," *Nature Reviews/Microbiology* 596:453-463.

Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.

Moennig, V. et al. (1992) "The Pestiviruses," *Advances in Virus Research* 41:53-98.

Neumann, A. (1998) "Hepatitis C Viral Dynamics in Vivo and the Antiviral Efficacy of Interferon-α Therapy," *Science* 282:103-107.

Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-α-2b Plus Ribavirin," *Drugs* 62:507-556.

International Search Report and Written Opinion for Application No. PCT/US2011/021279, mailed May 2, 2011.

International Search Report and Written Opinion for Application No. PCT/US2011/021335, mailed Feb. 22, 2011.

International Search Report and Written Opinion for Application No. PCT/US2010/042394, mailed Sep. 29, 2010.

International Search Report and Written Opinion for PCT/US2010/047983 mailed Nov. 15, 2010.

International Search Report and Written Opinion for PCT/US2012/046741 mailed Aug. 22, 2012.

Office Action for U.S. Appl. No. 12/838,684, mailed Aug. 2, 2012.

Notice of Allowance for U.S. Appl. No. 13/392,467, mailed Sep. 21, 2012.

Notice of Allowance for U.S. Appl. No. 13/006,761, mailed Oct. 3, 2012.

International Search Report from PCT/US2013/054405 issued Sep. 17, 2013 by the European Patent Office.

SOLID FORMS OF AN ANTIVIRAL COMPOUND

CROSS REFERENCE TO RELATED APPLICATIONS

This application claims the benefit under 35 U.S.C. §119(e) to U.S. Provisional Application Ser. No. 61/684,297, filed on Aug. 17, 2012, the entirety of which is incorporated herein by reference.

BACKGROUND

The present disclosure relates generally to crystalline solid forms and amorphous solid form of the antiviral compound 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, processes for making the forms, and their therapeutic methods of use.

Hepatitis C is recognized as a chronic viral disease of the liver which is characterized by liver disease. Although drugs targeting the liver are in wide use and have shown effectiveness, toxicity and other side effects have limited their usefulness Inhibitors of hepatitis C virus (HCV) are useful to limit the establishment and progression of infection by HCV as well as in diagnostic assays for HCV.

The compound 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, designated herein as Compound I, is known to be an effective anti-HCV agent, as described for example in WO 2011/088345. However, Compound I was not heretofore known in any crystalline or amorphous solid form.

SUMMARY

The present disclosure fulfills these needs and others by providing amorphous and crystalline forms of Compound I, hydrates and solvates of Compound I. The disclosure also provides processes for making the crystalline forms and methods for using them in the treatment of HCV. Specifically, twelve crystalline solid forms of Compound I have been discovered through various screening techniques. Form II is an anhydrous crystalline form as it is stable and non-hygroscopic under ambient conditions. Other forms are hydrates, solvates, or desolvated forms. In addition to the crystalline forms described below, in one embodiment, the amorphous solid form is also provided.

One embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate (Compound I Form I) characterized by an X-ray powder diffractogram comprising at least three of the following peaks: 4.0, 7.3, 8.1, 17.9, or 21.8 °2θ±0.2 °2θ, as determined on a diffractometer using Cu-Kα radiation.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I Form II) characterized by an X-ray powder diffractogram comprising at least three of the following peaks: 5.5, 6.0, 16.9, 18.1, or 21.3 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate and/or solvate (Compound I Form III) characterized by an X-ray powder diffractogram comprising at least three of the following peaks: 4.1, 6.8, 8.9, 17.4, or 21.4 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate and/or solvate (Compound I Form IV), characterized by an X-ray powder diffractogram comprising at least three of the following peaks: 4.1, 7.0, 9.0, 17.7, and 21.8 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid solvate (Compound I Form V), characterized by an X-ray powder diffractogram comprising at least three of the following peaks: 4.2, 7.0, 7.8, 8.4, or 21.1 °2θ±0.2 °2θ, as determined on a diffractometer using Cu-Kα.

In one embodiment the solvate is selected from the group consisting of methyl tert-butyl ether (MTBE) solvate (Compound I Form V-MTBE), isopropyl alcohol (IPA) solvate (Compound I Form V-IPA), ethanol (EtOH) solvate (Compound I Form V-EtOH), methyl ethyl ketone solvate (MEK) solvate (Compound I Form V-MEK), and 2-methyl tetrahydrofuran (2-Me-THF) solvate (Compound I Form V-2-Me-THF).

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid diisopropyl ether solvate (Compound I Form VI), characterized by an X-ray powder diffractogram comprising at least three of the following peaks: 5.3, 7.0, 8.1, 17.2, 19.0 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid isopropyl alcohol solvate (Compound I Form VII), characterized by an X-ray powder diffractogram comprising at least three of the following peaks: 4.6, 5.9, 8.8, 9.3, or 21.5 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid monohydrate (Compound I Form VIII), characterized by an X-ray powder diffractogram comprising at least three of the following peaks: 3.8, 7.7, 7.9, 18.0, or 21.7 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid ethanol solvate (Compound I Form IX), characterized by an X-ray powder diffractogram comprising at least three of the following peaks: 4.3, 7.0, 7.7, 8.5, or 16.9 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]

carbonyl}amino]thiophene-2-carboxylic acid methyl ethyl ketone (Compound I Form X), characterized by an X-ray powder diffractogram comprising at least three of the following peaks: 6.9, 8.0, 15.7, 16.1, or 17.5 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I Form XI), characterized by an X-ray powder diffractogram comprising at least three of the following peaks: 5.4, 5.7, 7.0, 7.9, or 8.6 °2θ±0.2 °2θ, as determined on a diffractometer using Cu-Kα.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid ethanol solvate (Compound I Form XII), characterized by an X-ray powder diffractogram comprising at least three of the following peaks: 4.5, 6.4, 7.1, 8.5, or 8.9 °2θ±0.2 °2θ, as determined on a diffractometer using Cu-Kα.

One embodiment is directed to a method for treating a subject suffering from hepatitis C virus (HCV), comprising administering to the subject a therapeutically effective amount of a compound as described throughout.

In another embodiment is provided a pharmaceutical composition comprising a compound as described throughout and a pharmaceutically acceptable excipient.

In one embodiment is a process for making Compound I Form I, comprising contacting a 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with water and a solvent selected from the group consisting of acetonitrile, methanol, and acetone, whereby Compound I Form I is formed.

In another embodiment is a process for making Compound I Form II, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with acetonitrile, whereby Compound I Form II is formed.

In another embodiment is a process for making Compound I Form III, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form III is formed.

In another embodiment is a process for making Compound I Form IV, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form IV is formed.

In another embodiment is a process for making Compound I Form V-MTBE, Compound I Form V-IPA, Compound I Form V-EtOH, Compound I Form V-MEK, or Compound I Form V-2-Me-THF, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with a solvent or solvent mixture selected from the group consisting of methyl tert-butyl ether, isopropyl alcohol and water mixture, ethanol and water mixture, methyl ethyl ketone and heptane mixture, and 2-methyl tetrahydrofuran and heptane mixture, whereby Compound I Form V-MTBE, Compound I Form V-IPA, Compound I Form V-EtOH, Compound I Form V-MEK, or Compound I Form V-2-Me-THF, respectively, is formed.

In another embodiment is a process for making Compound I Form VI, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with diisopropyl ether, whereby Compound I Form VI is formed.

In another embodiment is a process for making Compound I Form VII, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with isopropyl alcohol, whereby Compound I Form VII is formed.

In another embodiment is a process for making Compound I Form VIII, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form VIII is formed.

In another embodiment is a process for making Compound I Form IX, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol, whereby Compound I Form IX is formed.

In another embodiment is a process for making Compound I Form X, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with methyl ethyl ketone, whereby Compound I Form X is formed.

In another embodiment is a process for making Compound I Form XI, comprising desolvating Compound I Form X, whereby Compound I Form XI is formed.

In another embodiment is a process for making Compound I Form XII, comprising contacting Compound I Form I with ethanol in water, whereby Compound I Form XII is formed.

DETAILED DESCRIPTION

Figure 1:
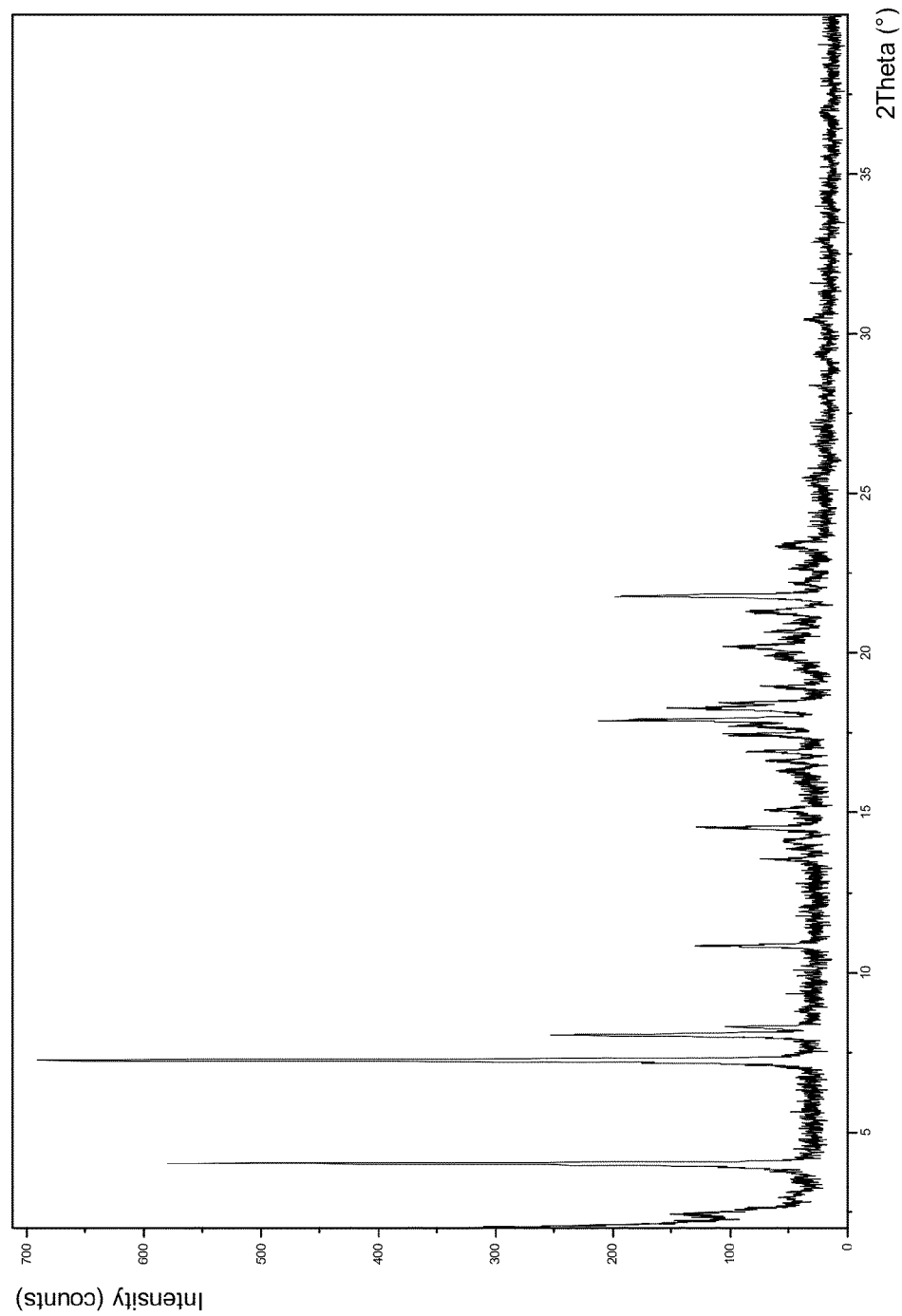
FIG. 1 is an X-ray powder diffraction pattern of Compound I Form I.

The compound 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I) is a selective and potent inhibitor of HCV NS5B.

Compound I

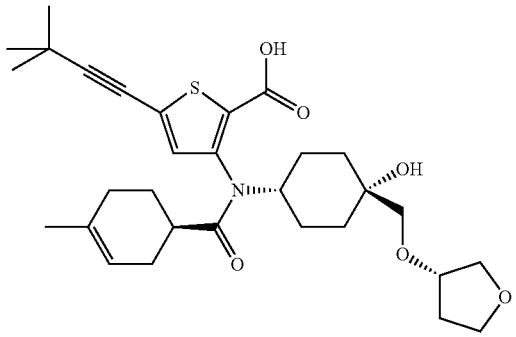

The present invention results from the surprising discoveries of the amorphous form and crystalline forms of Compound I, advantages attributed to the forms as described herein, and processes for making the crystalline forms. For example Form II is particularly desirable as it is contemplated to be stable during a wet granulation. Further, it is contemplated that the amorphous form has improved bioavailability.

DEFINITIONS

As used in the present specification, the following words and phrases are generally intended to have the meanings as set forth below, except to the extent that the context in which they are used indicates otherwise.

The term "hydrate" refers to a complex formed by the combining of Compound I and water. The term includes hemihydrates and channel hydrates.

The term "solvate" refers to a complex formed by the combining of Compound I and a solvent.

The term "desolvated" refers to a Compound I form that is a solvate as described herein, and from which solvent molecules have been partially or completely removed. Desolvation techniques to produce desolvated forms include, without limitation, exposure of a Compound I Form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

Any formula or structure given herein, including Compound I, is also intended to represent unlabeled forms as well as isotopically labeled forms of the compounds. Isotopically labeled compounds have structures depicted by the Formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes Compound I in which from 1 to "n" hydrogens attached to a carbon atom is/are replaced by deuterium, in which n is the number of hydrogens in the molecule. Such compounds exhibit increased resistance to metabolism and are thus useful for increasing the half life of any Compound I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

In addition, abbreviations as used herein have respective meanings as follows:

| | |
|---|---|
| 2-Me THF | 2 methyl tetrahydrofuran |
| Ac | Acetate |
| ACN | Acetonitrile |
| BippyPhos | 5-(di-tert-butylphosphino)-1',3',5'-triphenyl-1'H-[1,4']bipyrazole |
| Bn | Benzyl |
| br. s | Broad singlet |
| Bu | Butyl |
| dba | Dibenzylideneacetone |
| DCM | Dichloromethane |
| dd | Doublet of doublets |
| ddd | Doublet of doublet of doublets |
| DIPE | diisopropyl ether |
| DMF | Dimethylformamide |
| DMSO | Dimethylsulfoxide |
| dr | Diastereomeric ratio |
| DSC | Differential scanning calorimetry |
| DVS | Dynamic vapor sorption |
| ee | Enantiomeric excess |
| equiv | Equivalents |
| Et | Ethyl |
| EtOAc | Ethyl acetate |
| EtOH | Ethanol |
| ft | Foot (length) |
| g | Gram |
| GC | Gas chromatography |
| h | Hour |
| HCV | Hepatitis C virus |
| HPLC | High-pressure liquid chromatography |
| IPA | Isopropyl alcohol |
| IPAc | Isopropyl acetate |
| iPr | Isopropyl |
| iPrOAc | isopropyl acetate |
| kg | Kilogram |
| L | Liter |
| m | Multiplet |
| M | Molar |
| Me | Methyl |
| MeCl$_2$ | methylene chloride |
| MEK | methyl ethyl ketone |
| MeOH | methanol |
| mg | Milligram |
| MHz | Mega hertz |
| MIBK | Methylisobutyl ketone |
| min | Minute |
| mL | Milliliter |
| mmol | Millimole |
| mol | Mole |
| MTBE | Methyl-tert-butyl ether |
| N | Normal |
| NLT | No less than |
| NMR | Nuclear magnetic resonance |
| Ph | Phenyl |
| RH | Relative humidity |
| s | Singlet |
| t-Bu | tert-Butyl |
| td | Triplet of doublets |
| Tf | Trifluoromethanesulfonate |
| TGA | Thermogravimetric analysis |
| THF | Tetrahydrofuran |
| TMS | Trimethylsilyl |
| vol | Volume |
| wt | Weight |
| XRPD | X-ray powder diffraction |
| δ | Chemical shift |
| μL | Microliter |

Solid Forms of Compound I

One embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate (Compound I Form I) characterized by an X-ray powder diffractogram comprising at least three of the following peaks: 4.0, 7.3, 8.1, 17.9, or 21.8 °2θ±0.2 °2θ, as determined on a diffractometer using Cu-Kα radiation. In another embodiment, the diffractogram comprises peaks at 4.0, 7.3, 8.1, 17.9, and 21.8 °2θ±0.2 °2θ. In another embodiment, the diffractogram is substantially as shown in FIG. 1.

Figure 2:
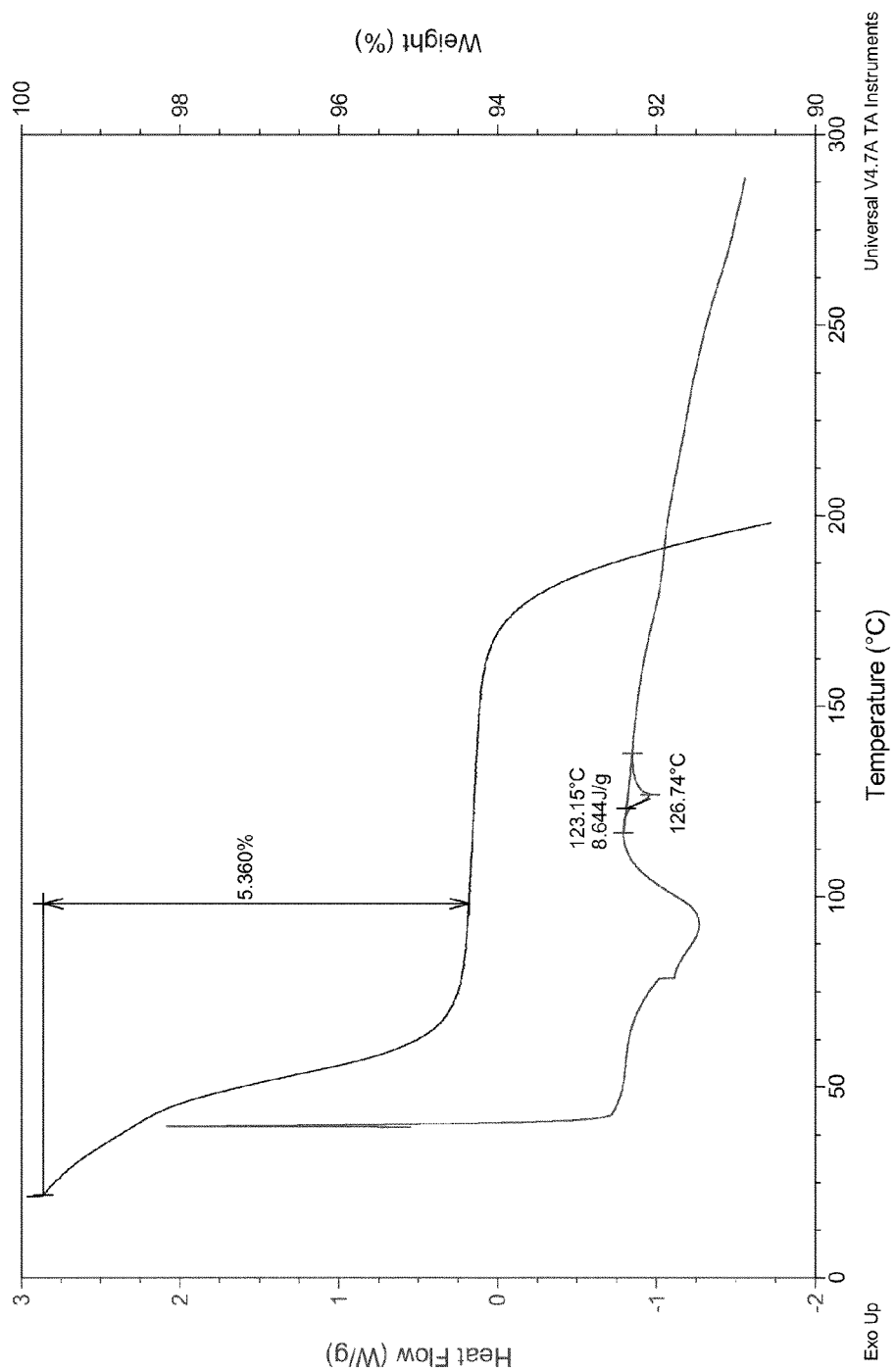
FIG. 2 is a combined differential scanning calorimetry plot (DSC; bottom curve) and thermogravimetric analysis (TGA; top curve) of Compound I Form I.

In one embodiment, Compound I Form I is characterized by a differential scanning calorimetry (DSC) curve that comprises two endotherms at about 55° C. to about 115° C. and about 127° C. In another embodiment, the DSC curve is substantially as shown in FIG. 2.

In one embodiment, Compound I Form I is characterized by a weight loss, as measured by thermogravimetric analysis (TGA), of about 5.4% at about 95° C. In one embodiment, the TGA is substantially as shown in FIG. 2.

Figure 4:
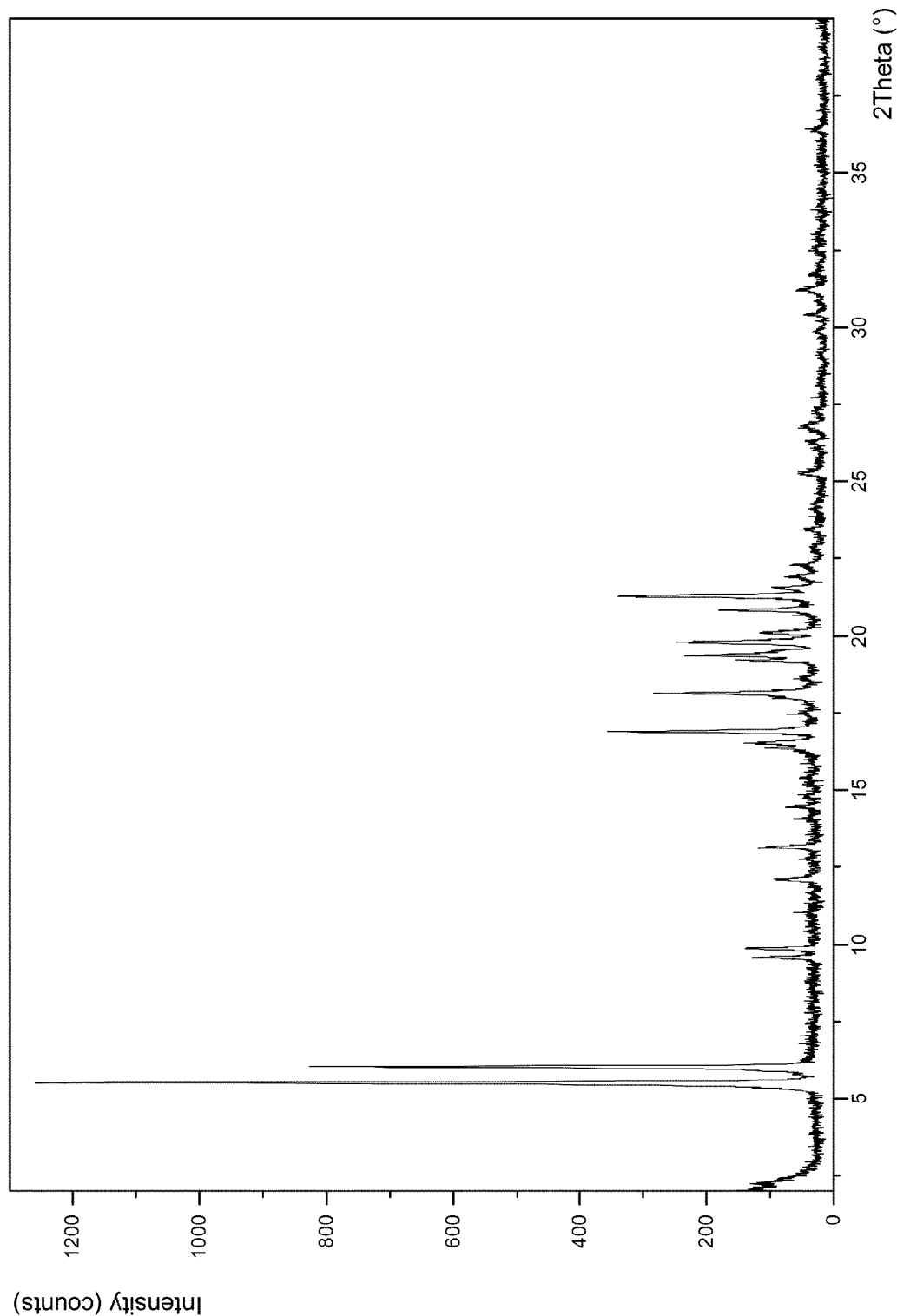
FIG. 4 is an X-ray powder diffraction pattern of Compound I Form II.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I Form II) characterized by an X-ray powder diffractogram comprising at least three of the following peaks: 5.5, 6.0, 16.9, 18.1, or 21.3 °2θ±0.2 °2θ, as determined on a diffractometer using Cu-Kα. In one embodiment, the diffractogram comprises peaks at 5.5, 6.0, 16.9, 18.1, and 21.3 °2θ±0.2 °2θ. In one embodiment, the diffractogram is substantially as shown in FIG. 4.

Figure 5:
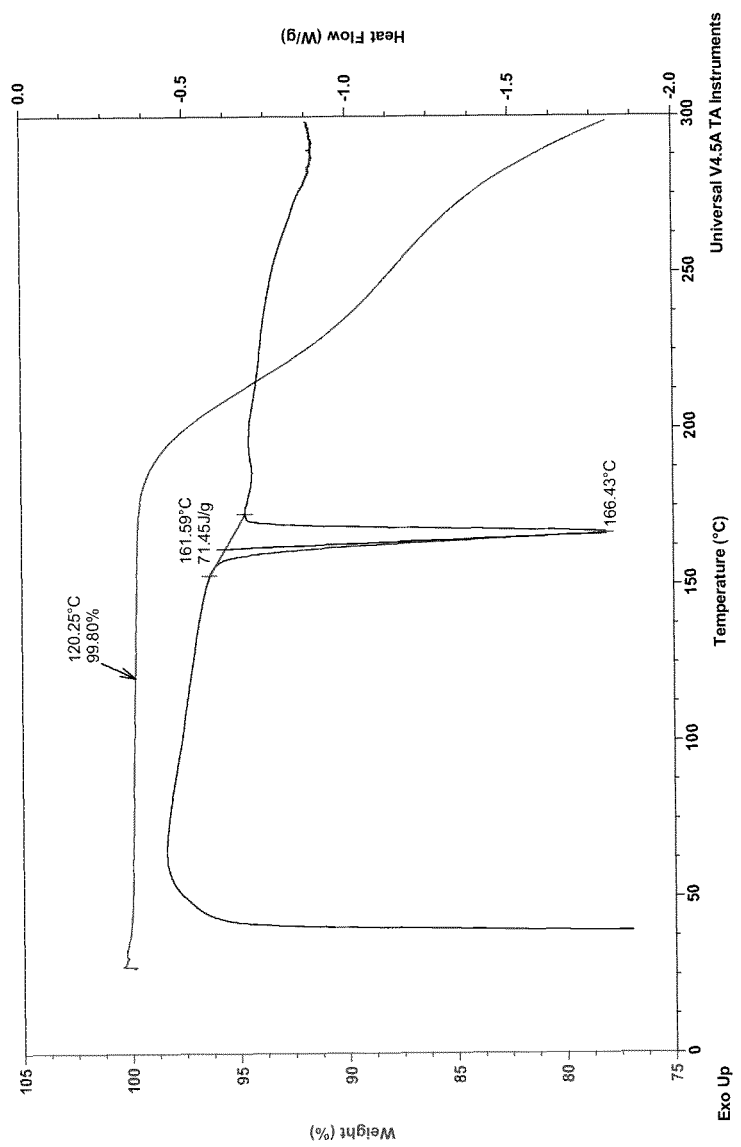
FIG. 5 is a combined differential scanning calorimetry plot (DSC; bottom curve) and thermogravimetric analysis (TGA; top curve) of Compound I Form II.

In one embodiment, Compound I Form II is characterized by a differential scanning calorimetry (DSC) curve that comprises an endotherm at about 162° C. In another embodiment, the DSC curve is substantially as shown in FIG. 5.

In one embodiment, Compound I Form II is characterized by a weight loss, as measured by thermogravimetric analysis (TGA), of about 0.2% at about 120° C. In one embodiment, the TGA is substantially as shown in FIG. 5.

Figure 8:
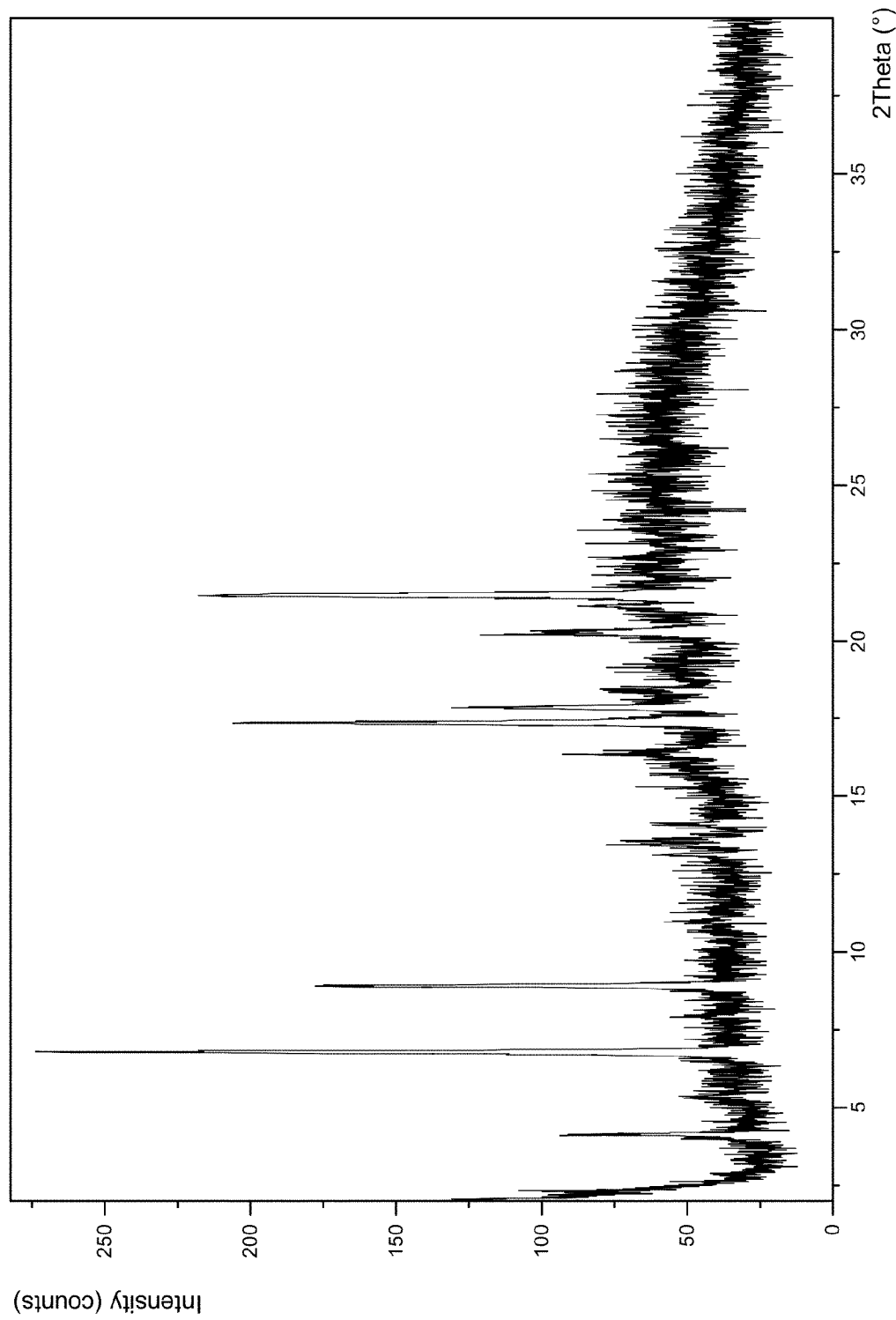
FIG. 8 is an X-ray powder diffraction pattern of Compound I Form III.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]

carbonyl}amino]thiophene-2-carboxylic acid hydrate and/or solvate (Compound I Form III) characterized by an X-ray powder diffractogram comprising at least three of the following peaks: 4.1, 6.8, 8.9, 17.4, or 21.4 °2θ±0.2 °2θ, as determined on a diffractometer using Cu-Kα. In one embodiment, the compound is a hydrate. In one embodiment, the compound is an ethanol solvate (Compound I Form III-EtOH). In one embodiment, the diffractogram comprises peaks at 4.1, 6.8, 8.9, 17.4, and 21.4 °2θ±0.2 °2θ. In one embodiment, the diffractogram is substantially as shown in FIG. 8.

Figure 9:
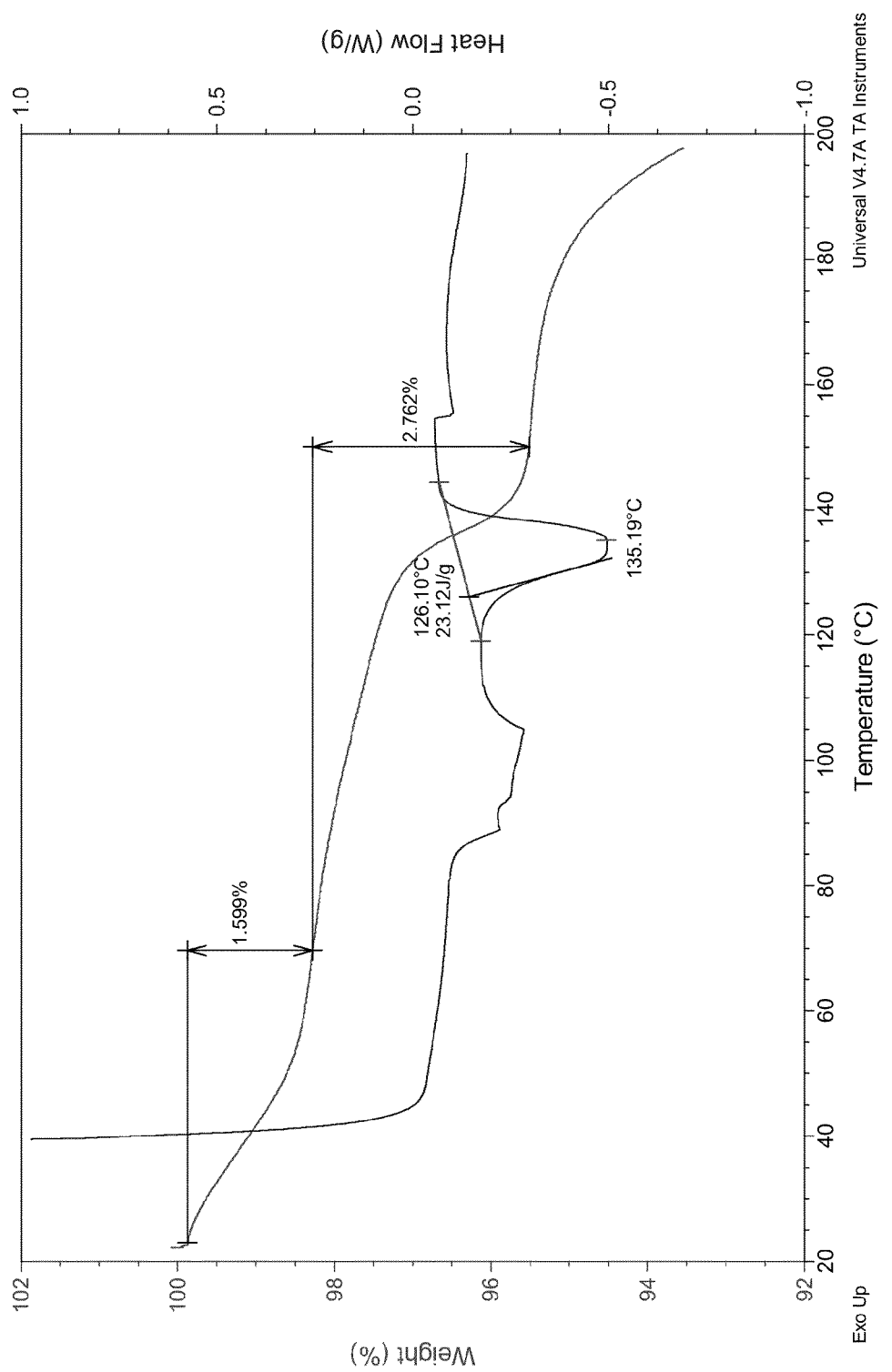
FIG. 9 is a combined differential scanning calorimetry plot (DSC; bottom curve) and thermogravimetric analysis (TGA; top curve) of Compound I Form III.

In one embodiment, Compound I Form III is characterized by a differential scanning calorimetry (DSC) curve that comprises two endotherms at about 80° C. to about 110° C. and about 135° C. In one embodiment, the DSC curve is substantially as shown in FIG. 9.

In one embodiment, Compound I Form III is characterized by two weight loss events, as measured by thermogravimetric analysis (TGA), of about 1.6% at about 70° C. and 2.8% at about 150° C. In one embodiment, the TGA is substantially as shown in FIG. 9.

Figure 10:
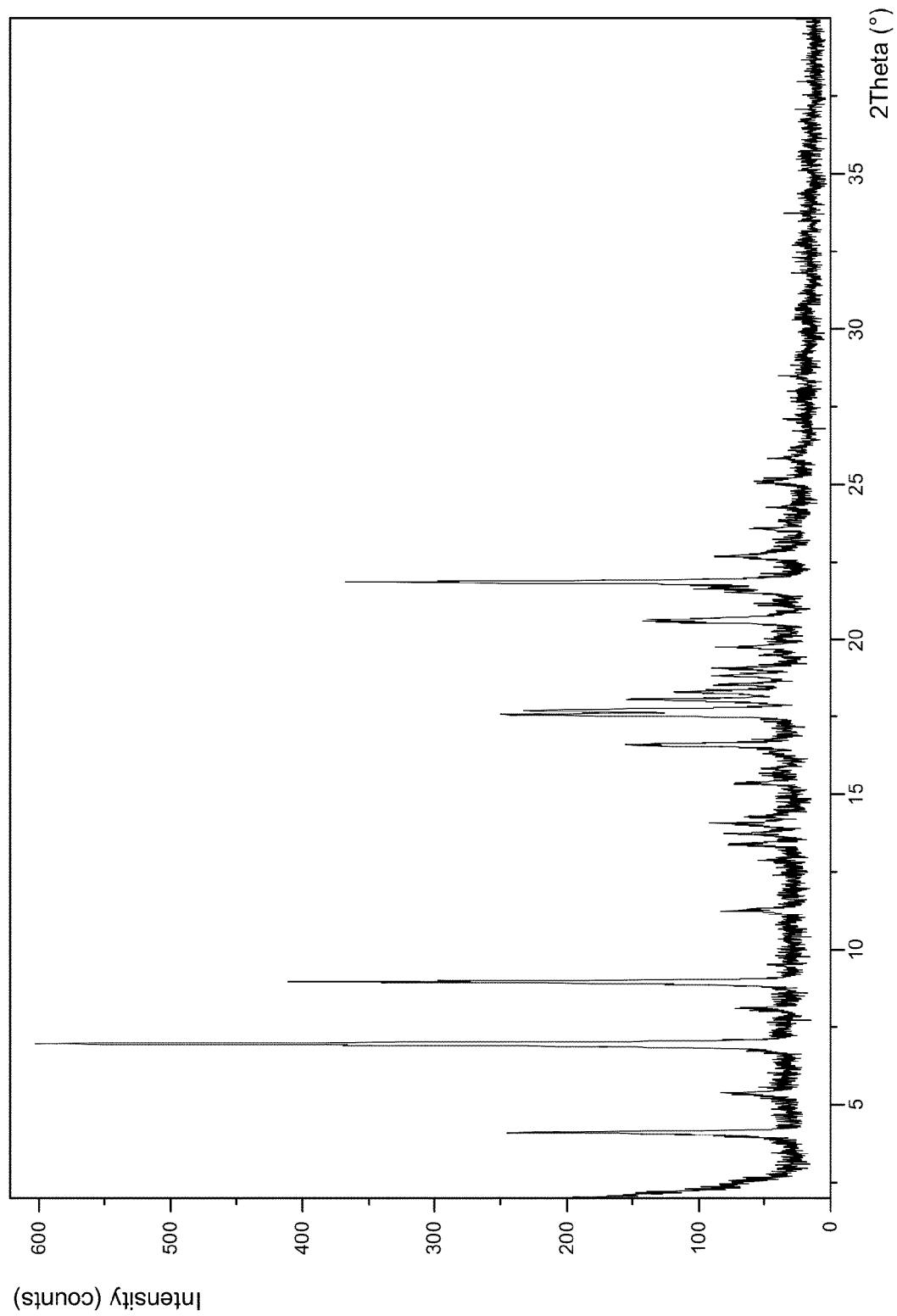
FIG. 10 is an X-ray powder diffraction pattern of Compound I Form IV.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate and/or solvate (Compound I Form IV), characterized by an X-ray powder diffractogram comprising at least three of the following peaks: 4.1, 7.0, 9.0, 17.7, and 21.8 °2θ±0.2 °2θ, as determined on a diffractometer using Cu-Kα. In one embodiment, the compound is a hydrate. In one embodiment, the compound is an ethanol solvate (Compound I Form IV-EtOH). In one embodiment, the diffractogram comprises peaks at 4.1, 7.0, 9.0, 17.7, and 21.8 °2θ±0.2 °2θ. In one embodiment, the diffractogram is substantially as shown in FIG. 10.

Figure 11:
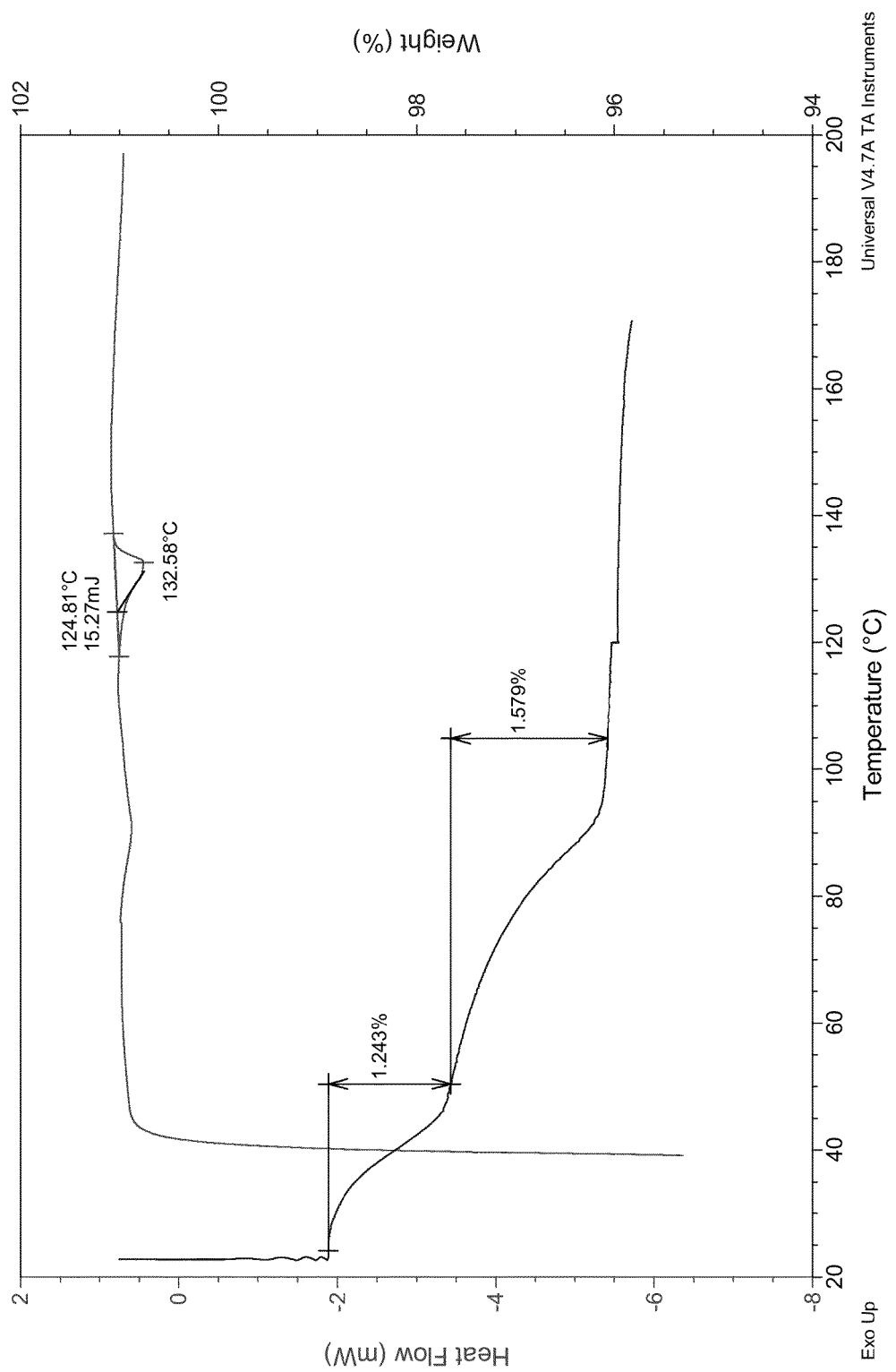
FIG. 11 is a combined differential scanning calorimetry plot (DSC; top curve) and thermogravimetric analysis (TGA; bottom curve) of Compound I Form IV.

In one embodiment, Compound I Form IV is characterized by a differential scanning calorimetry (DSC) curve that comprises two endotherms at about 78 to about 110° C. and about 133° C. In one embodiment, the DSC curve is substantially as shown in FIG. 11.

In one embodiment, Compound I Form IV is characterized by two weight loss events, as measured by thermogravimetric analysis (TGA), of about 1.2% at about 50° C. and 1.6% at about 100° C. In one embodiment, the TGA is substantially as shown in FIG. 11.

Figure 12:
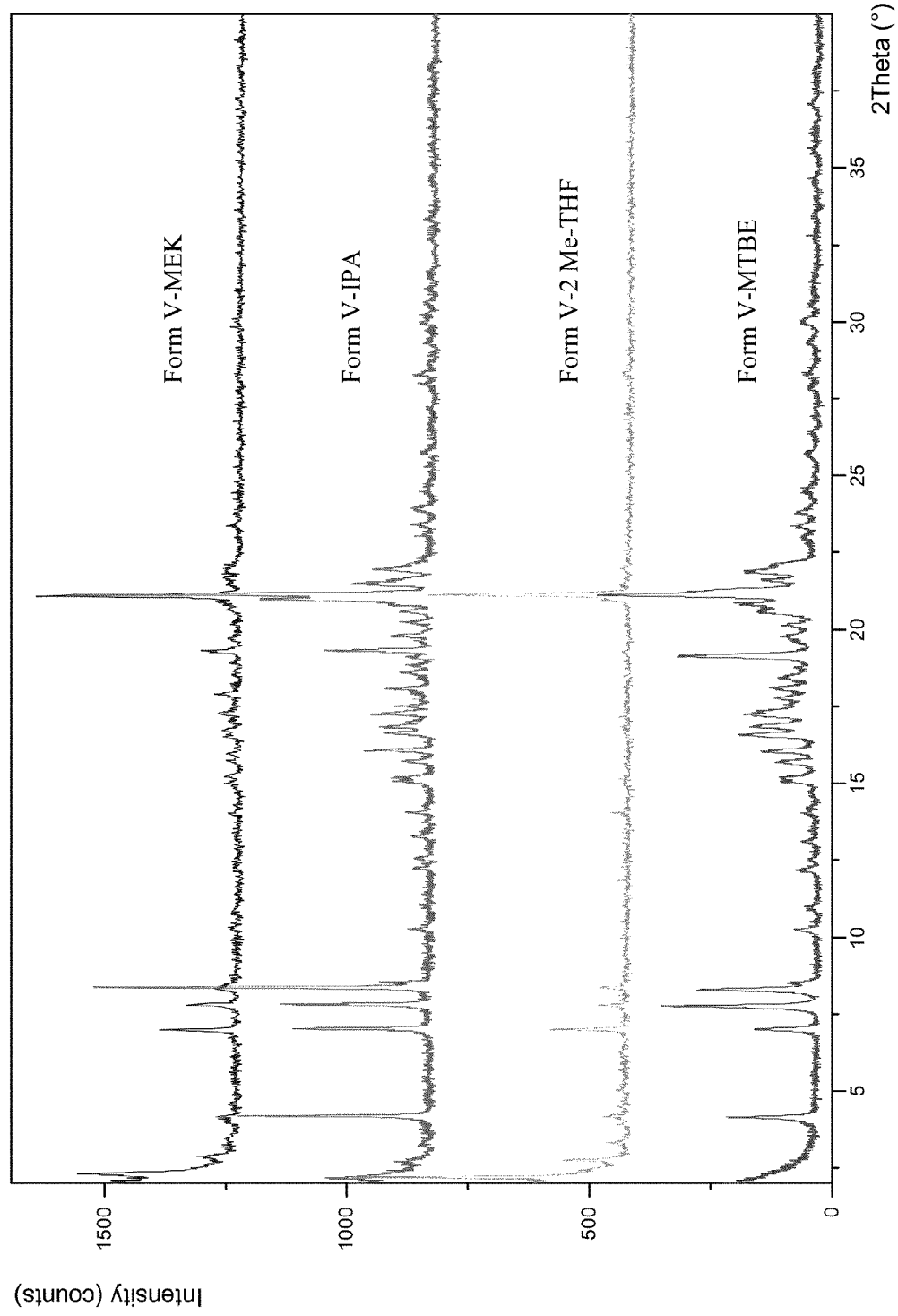
FIG. 12 is an X-ray powder diffraction pattern of Compound I Form V, obtained from MTBE, IPA/water, MEK/heptane, 2-Me-THF/heptane.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid solvate (Compound I Form V), characterized by an X-ray powder diffractogram comprising at least three of the following peaks: 4.2, 7.0, 7.8, 8.4, or 21.1 °2θ±0.2 °2θ, as determined on a diffractometer using Cu-Kα. The solvate is selected from the group consisting of methyl tert-butyl ether (MTBE) solvate (Compound I Form V-MTBE), isopropyl alcohol (IPA) solvate (Compound I Form V-IPA), ethanol (EtOH) solvate (Compound I Form V-EtOH), methyl ethyl ketone solvate (MEK) solvate (Compound I Form V-MEK), and 2-methyl tetrahydrofuran (2-Me-THF) solvate (Compound I Form V-2-Me-THF). In one embodiment, the diffractogram comprises peaks at 4.2, 7.0, 7.8, 8.4, and 21.1 °2θ±0.2 °2θ. In one embodiment, the diffractogram is substantially as shown in FIG. 12.

Figure 13:
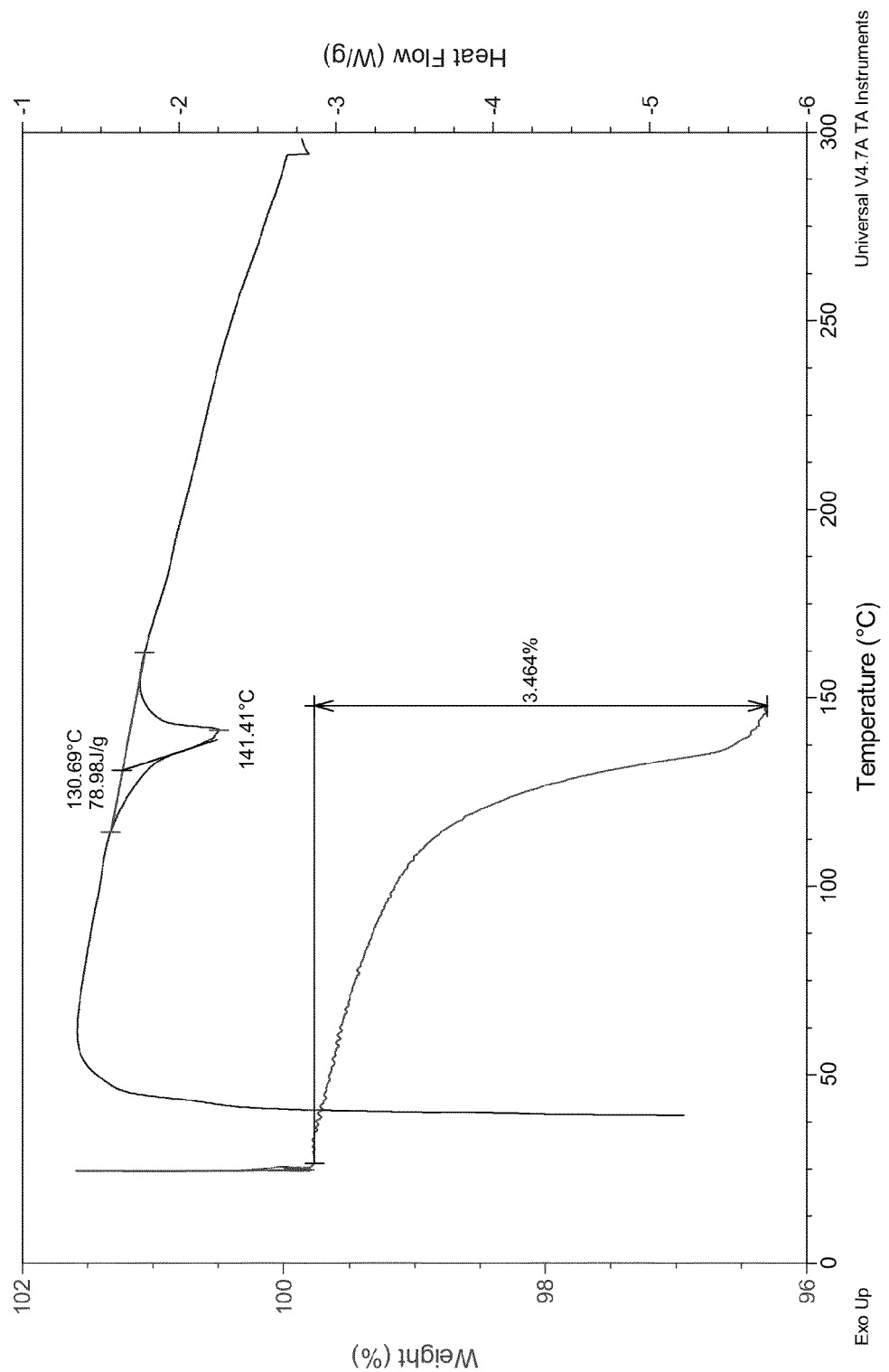
FIG. 13 is a combined differential scanning calorimetry plot (DSC; top curve) and thermogravimetric analysis (TGA; bottom curve) of Compound I Form V.

In one embodiment, Compound I Form V-EtOH is characterized by a differential scanning calorimetry (DSC) curve that comprises an endotherm at about 133° C. to about 141° C. In one embodiment, the DSC curve is substantially as shown in FIG. 13.

In one embodiment, Compound I Form V is characterized by a weight loss, as measured by thermogravimetric analysis (TGA), of about 4.8% at about 120° C. for Compound I Form V-MTBE, 4.2% at about 130° C. for Compound I Form V-IPA, and 3.5% at about 140° C. for Compound I Form V-EtOH. In one embodiment, the TGA is substantially as shown in FIG. 13.

Figure 14:
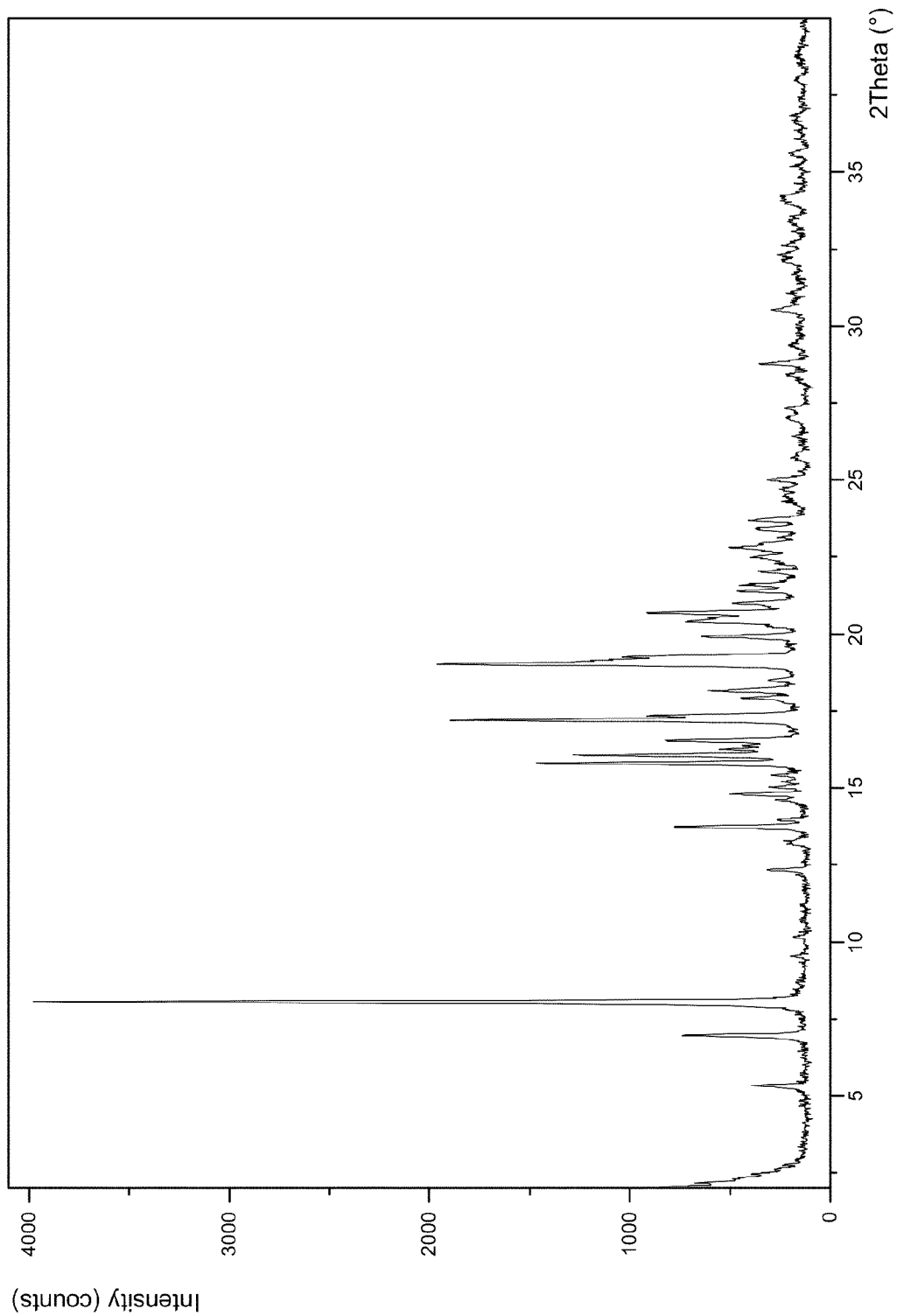
FIG. 14 is an X-ray powder diffraction pattern of Compound I Form VI.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid diisopropyl ether solvate (Compound I Form VI), characterized by an X-ray powder diffractogram comprising at least three of the following peaks: 5.3, 7.0, 8.1, 17.2, 19.0 °2θ±0.2 °2θ, as determined on a diffractometer using Cu-Kα. In one embodiment, the diffractogram comprises peaks at 5.3, 7.0, 8.1, 17.2, and 19.0 °2θ±0.2 °2θ. In one embodiment, the diffractogram is substantially as shown in FIG. 14.

Figure 15:
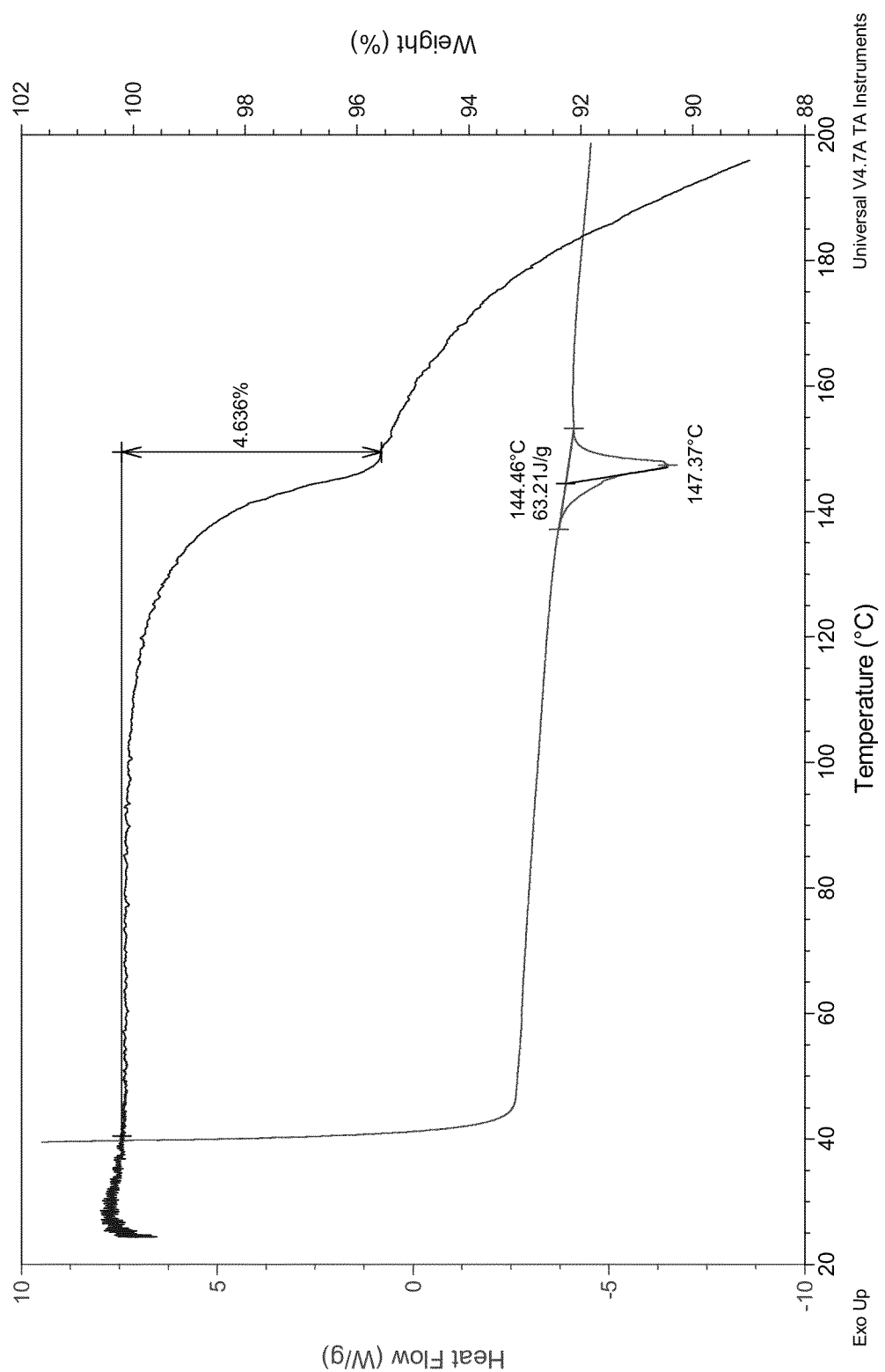
FIG. 15 is a combined differential scanning calorimetry plot (DSC; bottom curve) and thermogravimetric analysis (TGA; top curve) of Compound I Form VI.

In one embodiment, Compound I Form VI is characterized by a differential scanning calorimetry (DSC) curve that comprises an endotherm at about 147° C. In one embodiment, the DSC curve is substantially as shown in FIG. 15.

In one embodiment, Compound I Form VI is characterized by a weight loss, as measured by thermogravimetric analysis (TGA), of about 4.6% at about 150° C. In one embodiment, the TGA is substantially as shown in FIG. 15.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid isopropyl alcohol solvate (Compound I Form VII), characterized by an X-ray powder diffractogram comprising at least three of the following peaks: 4.6, 5.9, 8.8, 9.3, or 21.5 °2θ±0.2 °2θ, as determined on a diffractometer using Cu-Kα.

Figure 16:
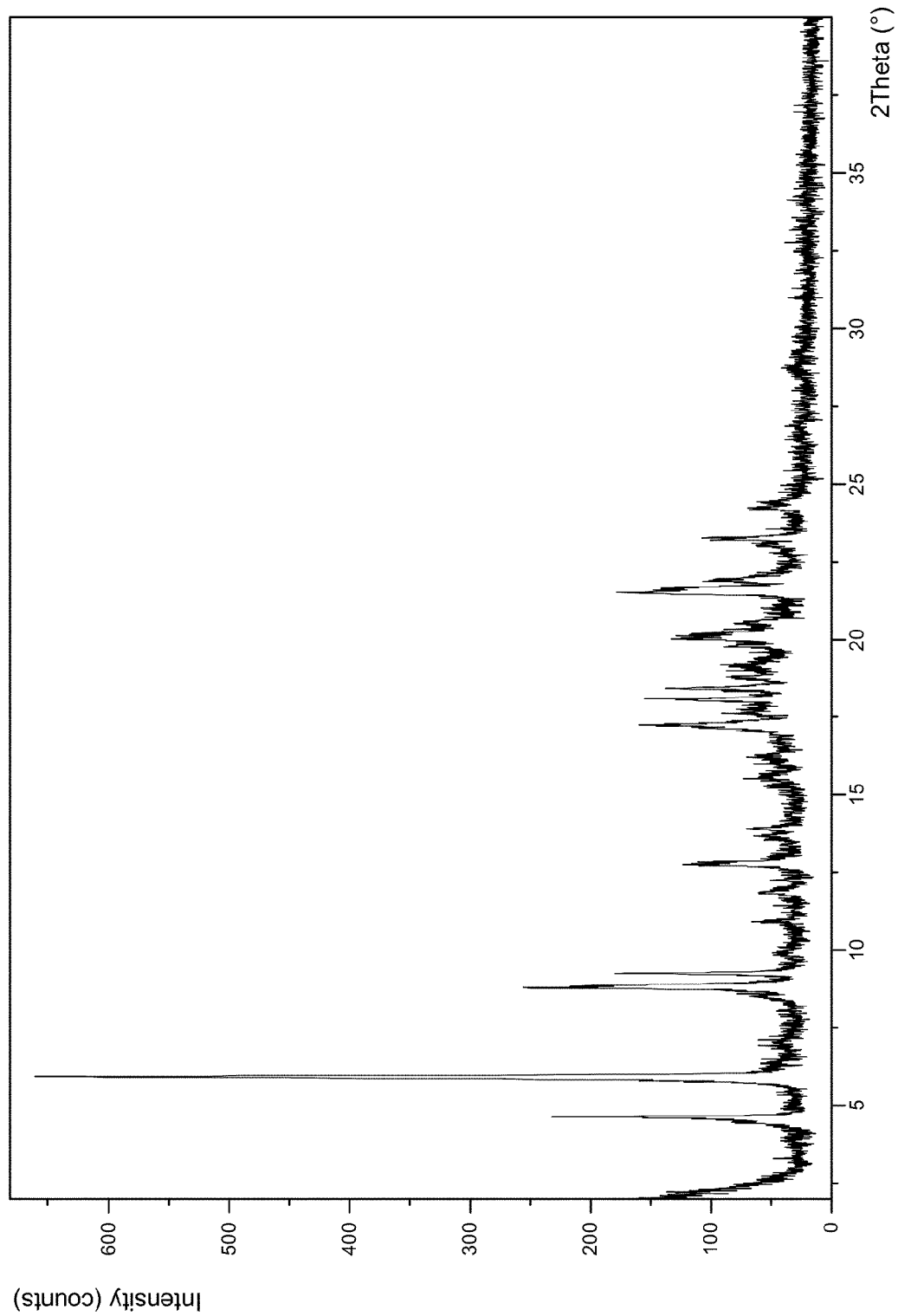
FIG. 16 is an X-ray powder diffraction pattern of Compound I Form VII.

In one embodiment, the diffractogram comprises peaks at 4.6, 5.9, 8.8, 9.3, and 21.5 °2θ±0.2 °2θ. In one embodiment, the diffractogram is substantially as shown in FIG. 16.

Figure 17:
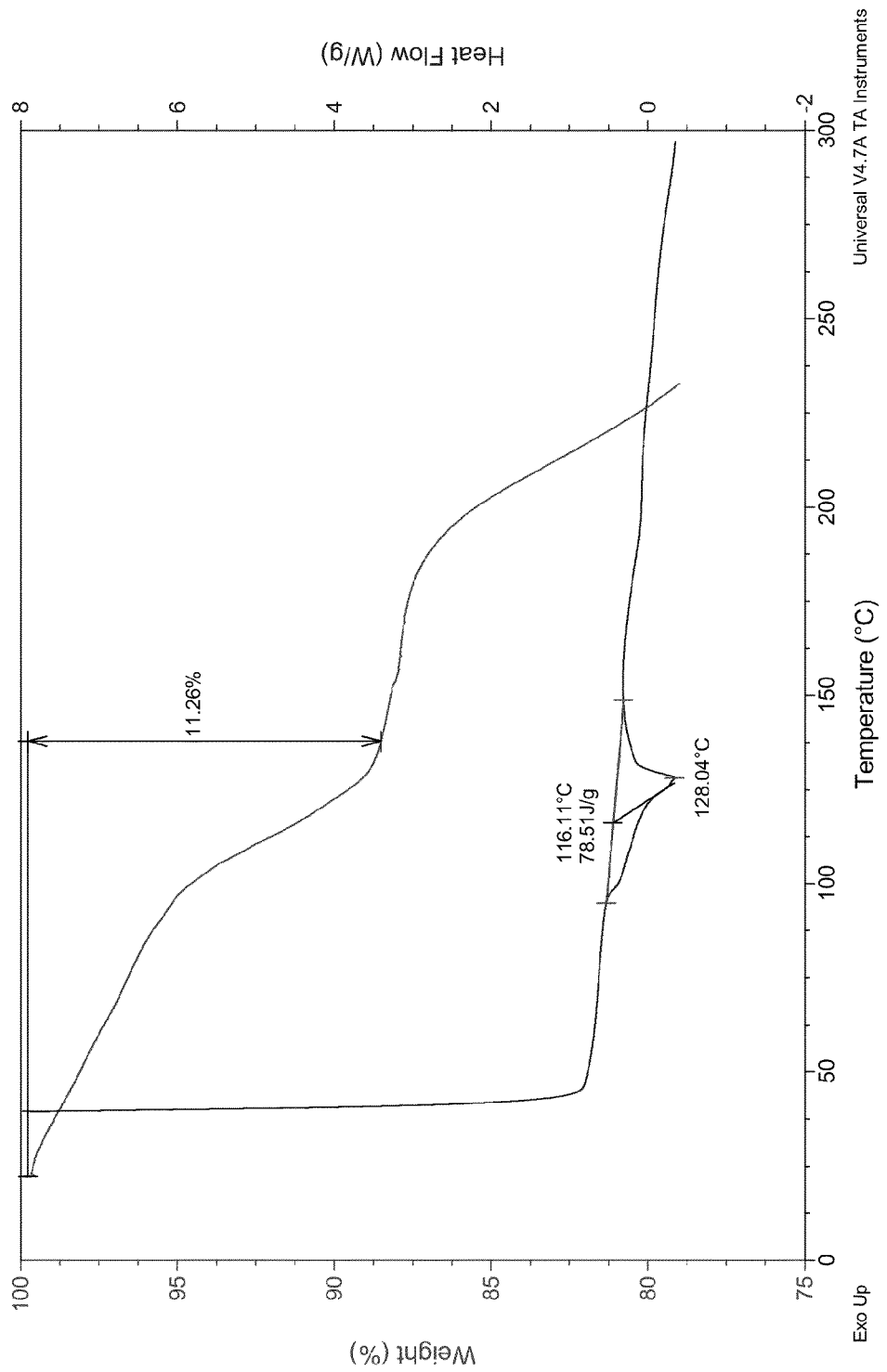
FIG. 17 is a combined differential scanning calorimetry plot (DSC; bottom curve) and thermogravimetric analysis (TGA; top curve) of Compound I Form VII.

In one embodiment, Compound I Form VII is characterized by a differential scanning calorimetry (DSC) curve that comprises an endotherm at about 128° C. In one embodiment, the DSC curve is substantially as shown in FIG. 17.

In one embodiment, Compound I Form VII is characterized by a weight loss, as measured by thermogravimetric analysis (TGA), of about 11.3% at about 140° C. In one embodiment, the TGA is substantially as shown in FIG. 17.

Figure 18:
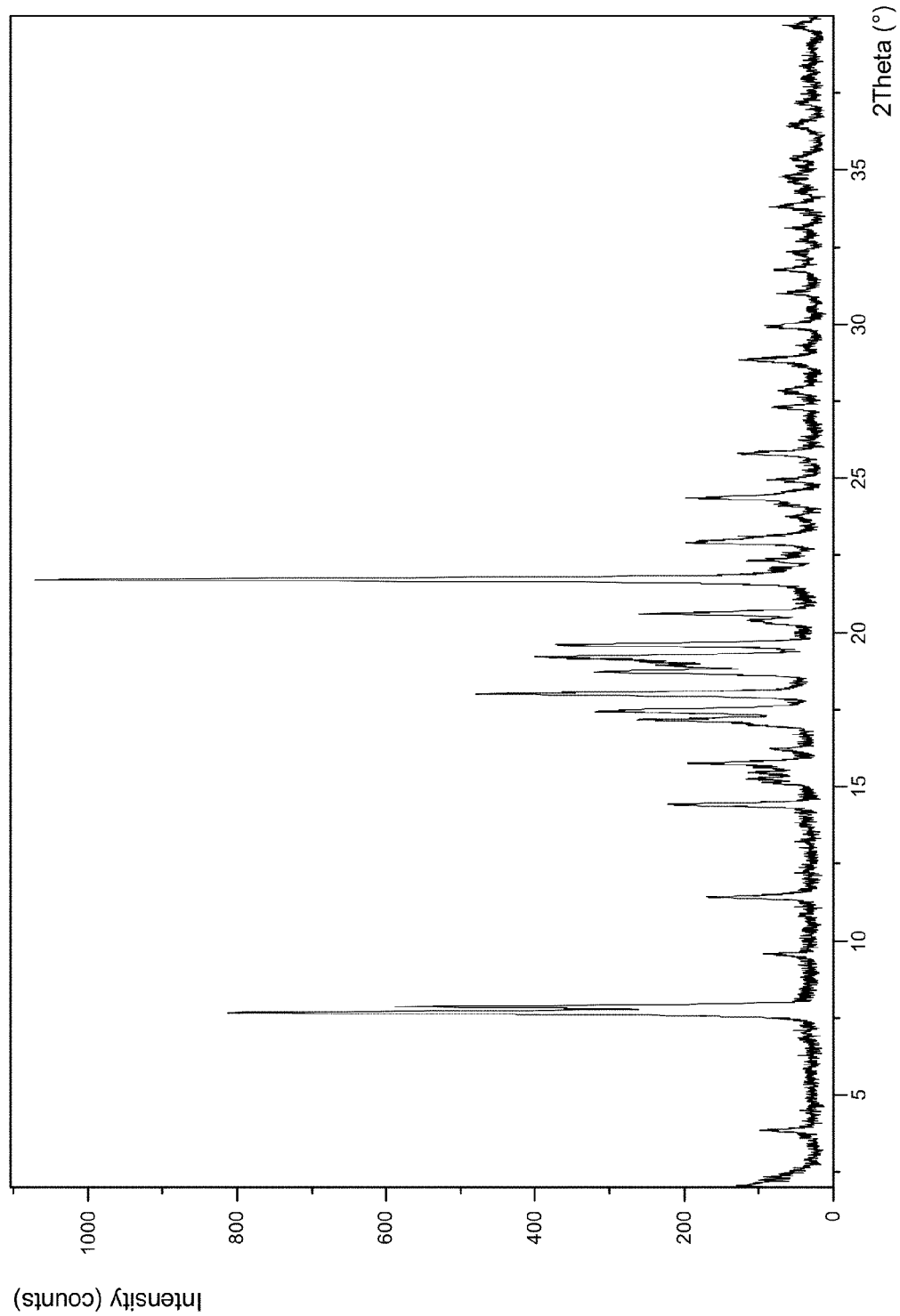
FIG. 18 is an X-ray powder diffraction pattern of Compound I Form VIII.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid monohydrate (Compound I Form VIII), characterized by an X-ray powder diffractogram comprising at least three of the following peaks: 3.8, 7.7, 7.9, 18.0, or 21.7 °2θ±0.2 °2θ, as determined on a diffractometer using Cu-Kα. In one embodiment, the diffractogram comprises peaks at 3.8, 7.7, 7.9, 18.0, and 21.7 °2θ±0.2 °2θ. In one embodiment, the diffractogram is substantially as shown in FIG. 18.

Figure 19:
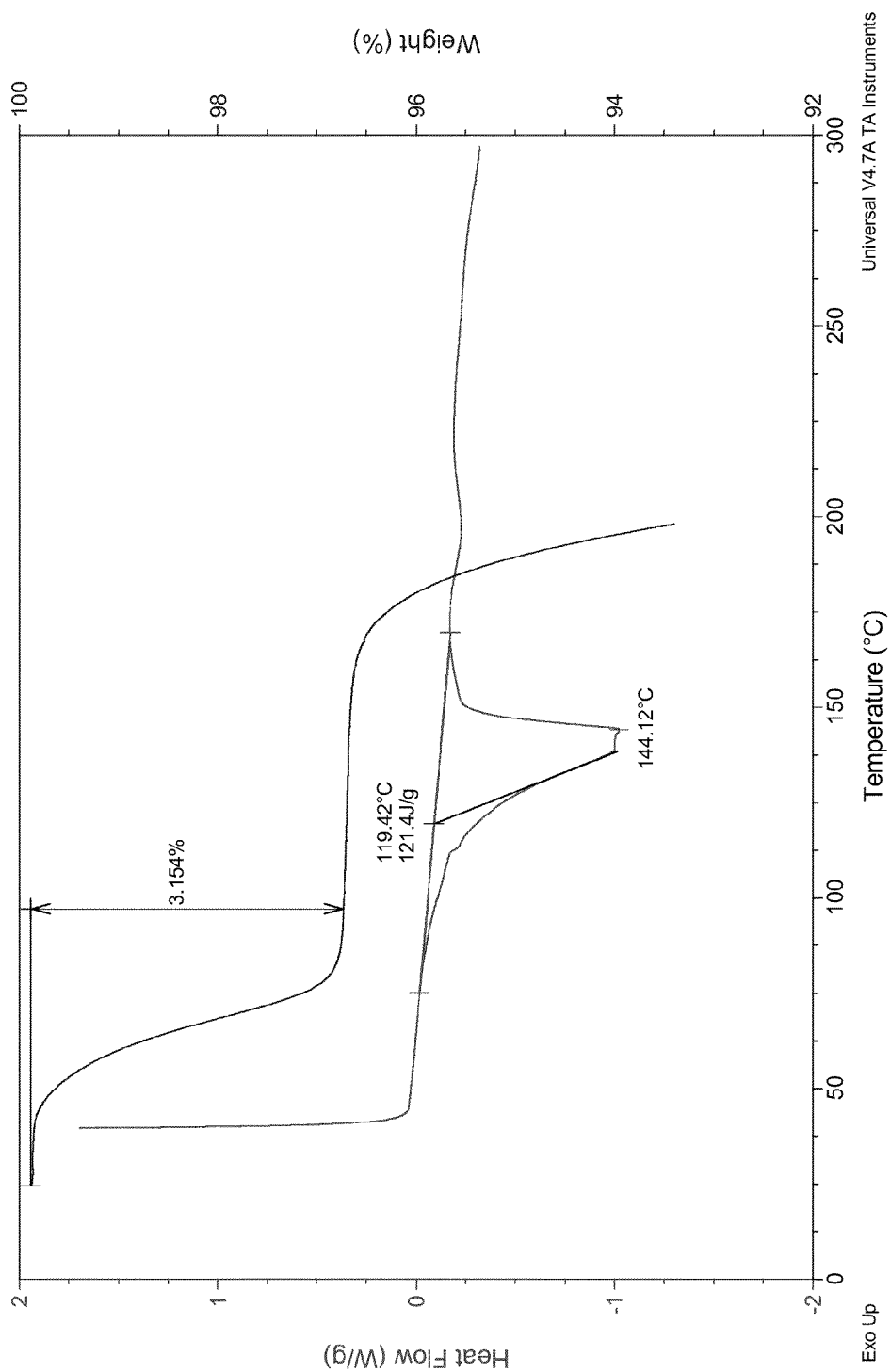
FIG. 19 is a combined differential scanning calorimetry plot (DSC; bottom curve) and thermogravimetric analysis (TGA; top curve) of Compound I Form VIII

In one embodiment, Compound I Form VIII is characterized by a differential scanning calorimetry (DSC) curve that comprises an endotherm at about 144° C. In one embodiment, the DSC curve is substantially as shown in FIG. 19.

In one embodiment, Compound I Form VIII is characterized by a weight loss, as measured by thermogravimetric analysis (TGA), of about 3.2% at about 100° C. In one embodiment, the TGA is substantially as shown in FIG. 19.

Figure 20:
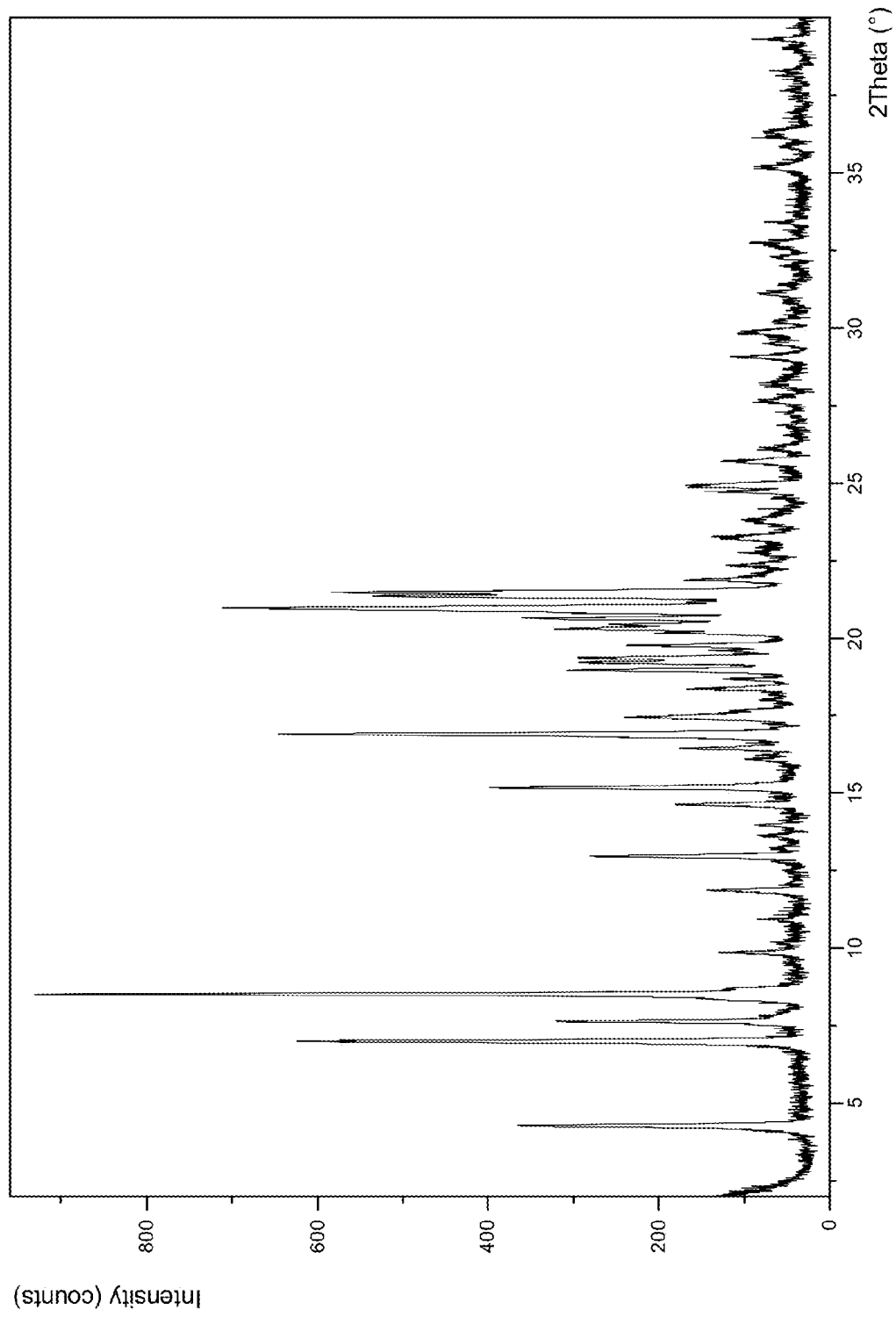
FIG. 20 is an X-ray powder diffraction pattern of Compound I Form IX.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]

carbonyl}amino]thiophene-2-carboxylic acid ethanol solvate (Compound I Form IX), characterized by an X-ray powder diffractogram comprising at least three of the following peaks: 4.3, 7.0, 7.7, 8.5, or 16.9 °2θ±0.2 °2θ, as determined on a diffractometer using Cu-Kα. In one embodiment, the diffractogram comprises peaks at 4.3, 7.0, 7.7, 8.5, and 16.9 °2θ±0.2 °2θ. In one embodiment, the diffractogram is substantially as shown in FIG. 20.

Figure 21:
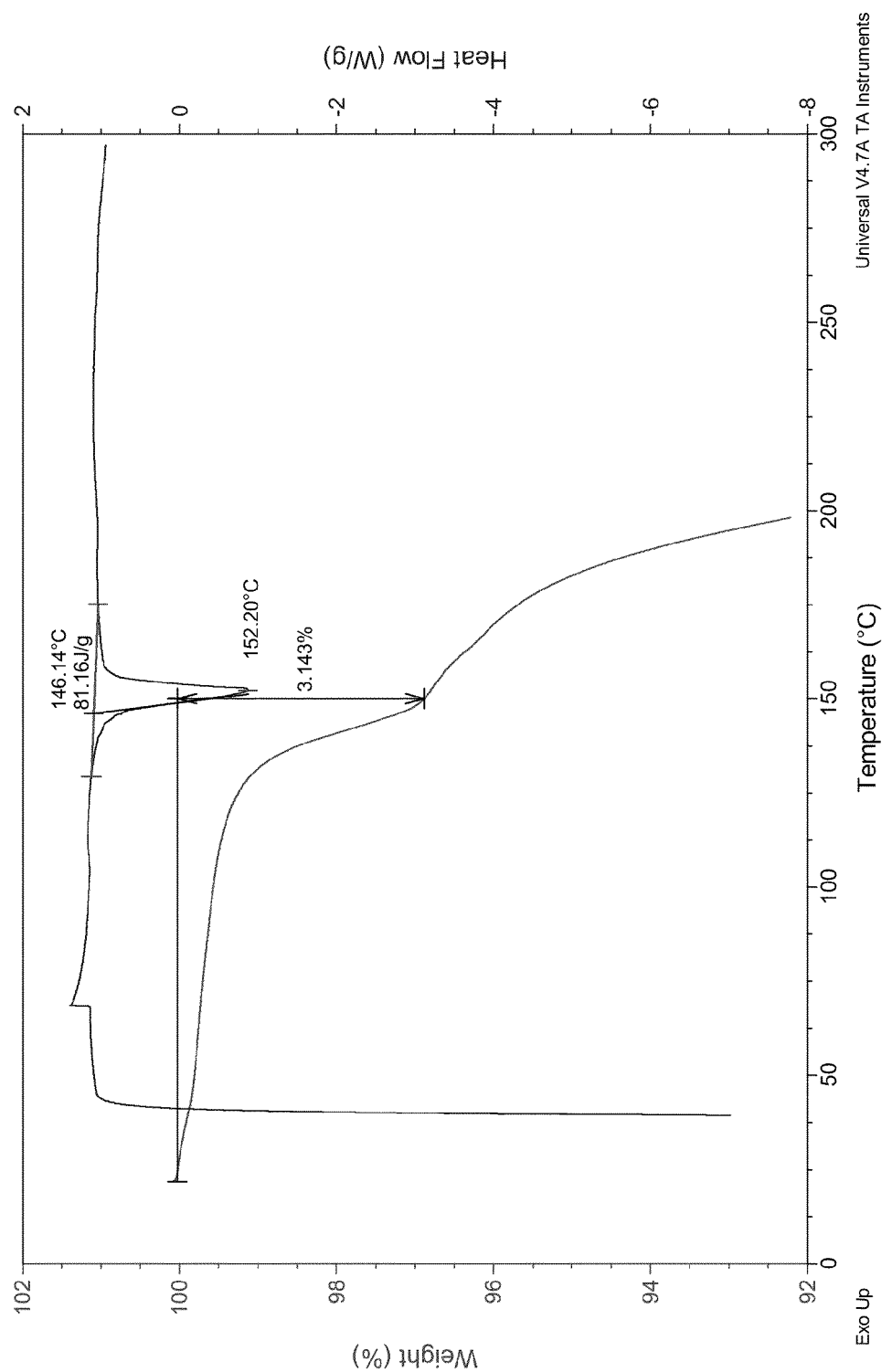
FIG. 21 is a combined differential scanning calorimetry plot (DSC; top curve) and thermogravimetric analysis (TGA; bottom curve) of Compound I Form IX

In one embodiment, Compound I Form IX is characterized by a differential scanning calorimetry (DSC) curve that comprises an endotherm at about 152° C. In one embodiment, the DSC curve is substantially as shown in FIG. 21.

In one embodiment, Compound I Form IX is characterized by a weight loss, as measured by thermogravimetric analysis (TGA), of about 3.1% at about 150° C. In one embodiment, the TGA is substantially as shown in FIG. 21.

Figure 22:
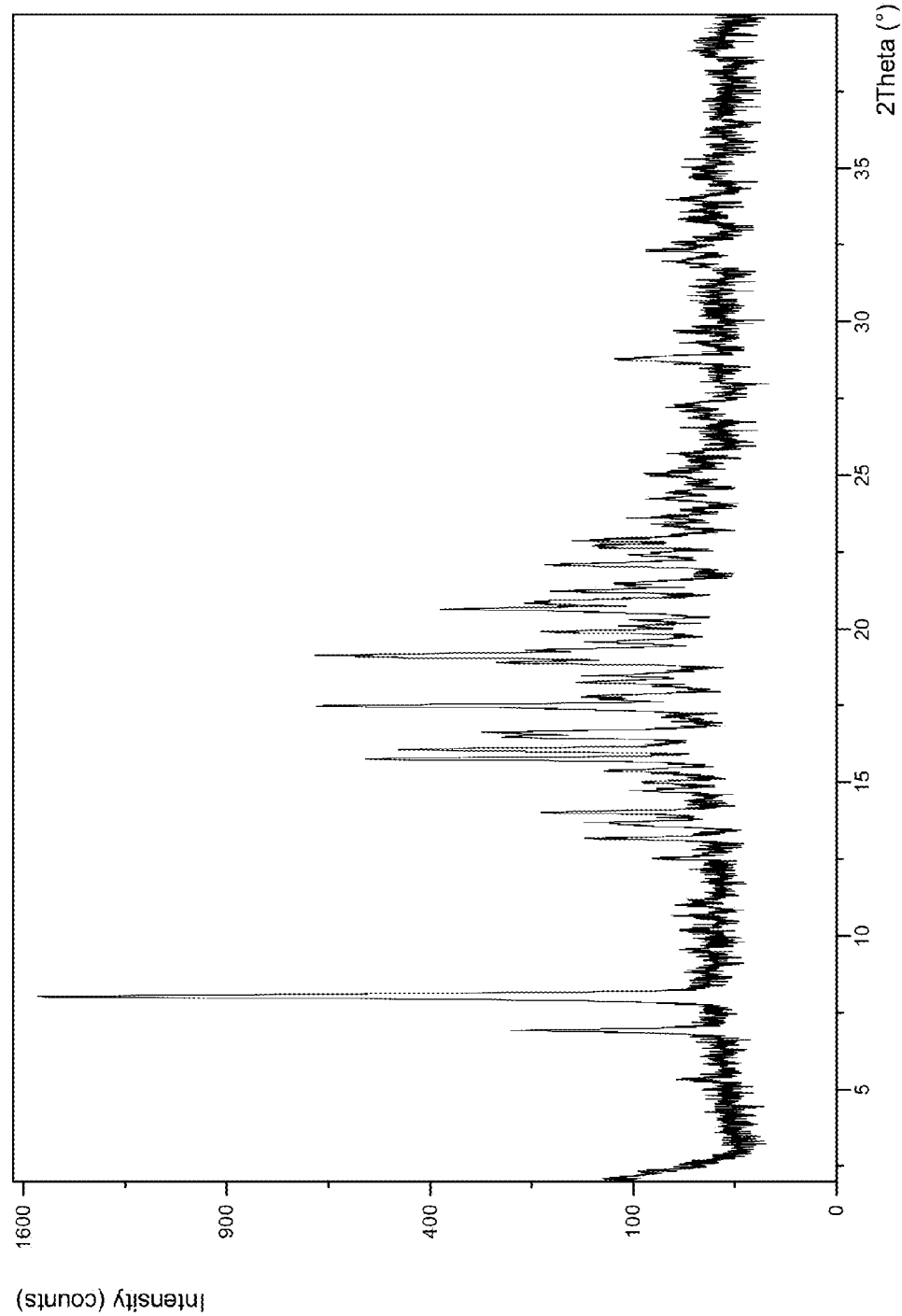
FIG. 22 is an X-ray powder diffraction pattern of Compound I Form X.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid methyl ethyl ketone (Compound I Form X), characterized by an X-ray powder diffractogram comprising at least three of the following peaks: 6.9, 8.0, 15.7, 16.1, or 17.5 °2θ±0.2 °2θ, as determined on a diffractometer using Cu-Kα. In one embodiment, the diffractogram comprises peaks at 6.9, 8.0, 15.7, 16.1, and 17.5 °2θ±0.2 °2θ. In one embodiment, the diffractogram is substantially as shown in FIG. 22.

Figure 23:
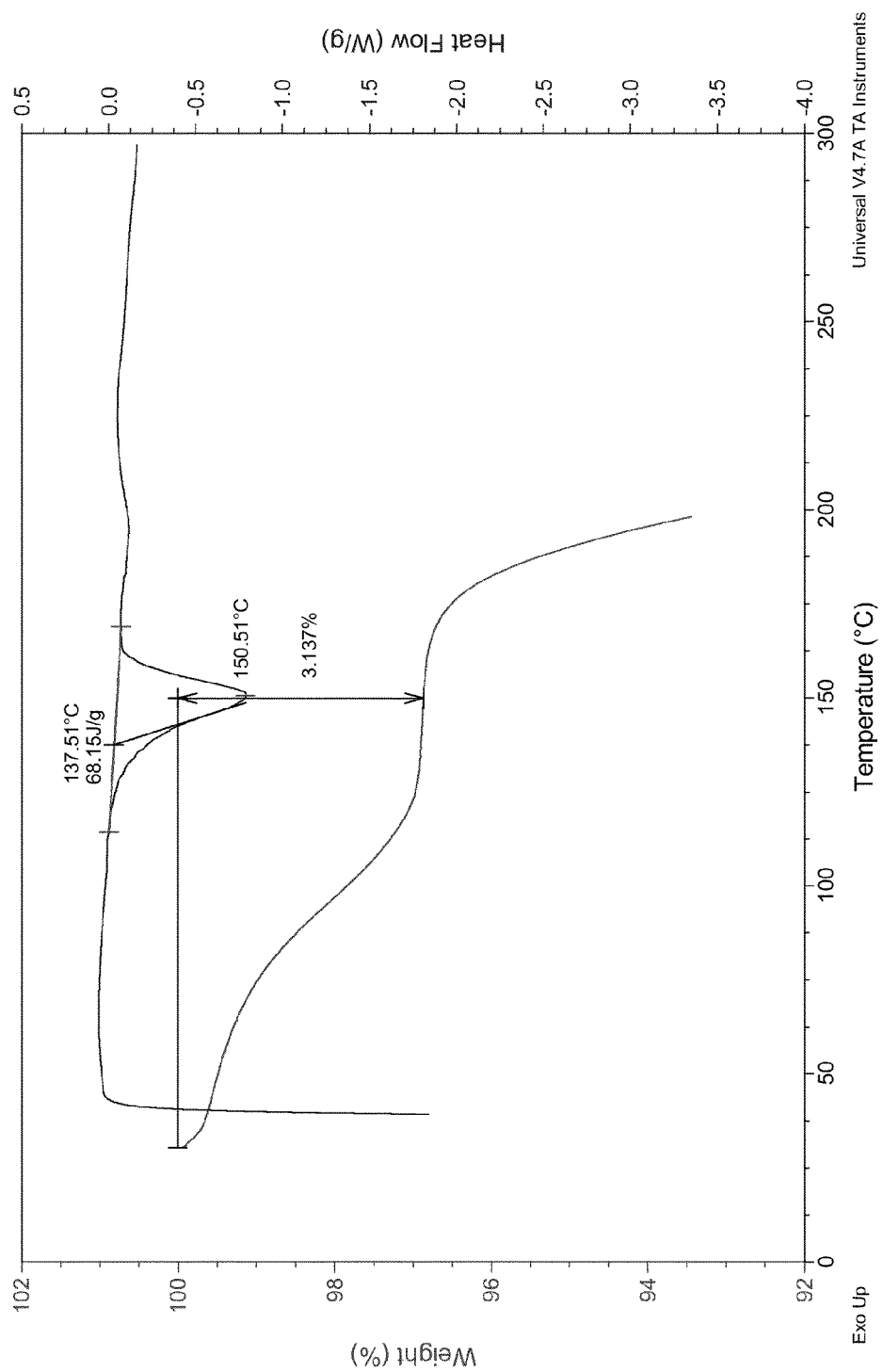
FIG. 23 is a combined differential scanning calorimetry plot (DSC; top curve) and thermogravimetric analysis (TGA; bottom curve) of Compound I Form X.

In one embodiment, Compound I Form X is characterized by a differential scanning calorimetry (DSC) curve that comprises an endotherm at about 150° C. In one embodiment, the DSC curve is substantially as shown in FIG. 23.

In one embodiment, Compound I Form X is characterized by a weight loss, as measured by thermogravimetric analysis (TGA), of about 3.1% at about 150° C. In one embodiment, the TGA is substantially as shown in FIG. 23.

Figure 24:
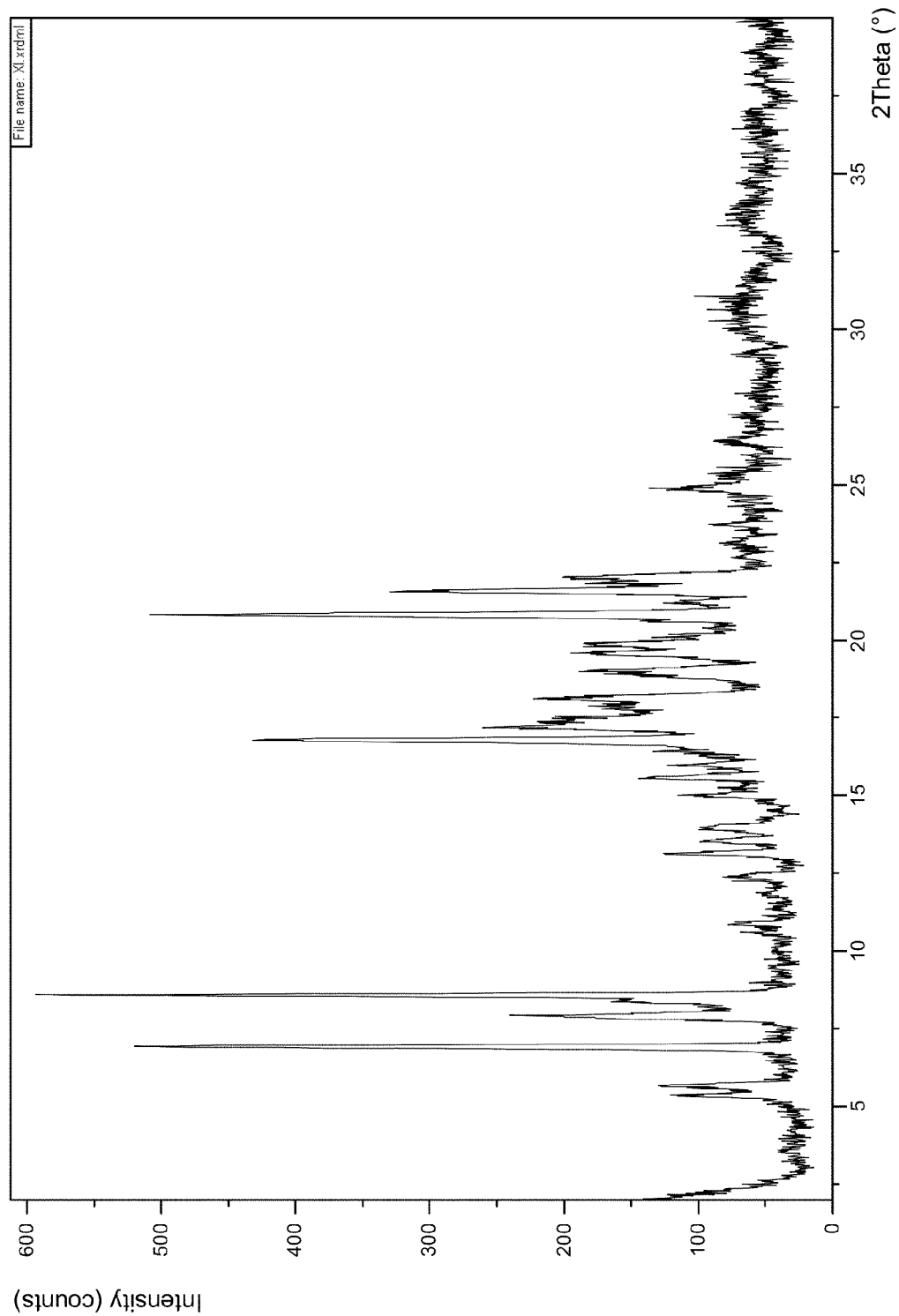
FIG. 24 is an X-ray powder diffraction pattern of Compound I Form XI.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I Form XI), characterized by an X-ray powder diffractogram comprising at least three of the following peaks: 5.4, 5.7, 7.0, 7.9, or 8.6 °2θ±0.2 °2θ, as determined on a diffractometer using Cu-Kα. In one embodiment, the diffractogram comprises peaks at 5.4, 5.7, 7.0, 7.9, and 8.6 °2θ±0.2 °2θ. In one embodiment, the diffractogram is substantially as shown in FIG. 24.

Figure 25:
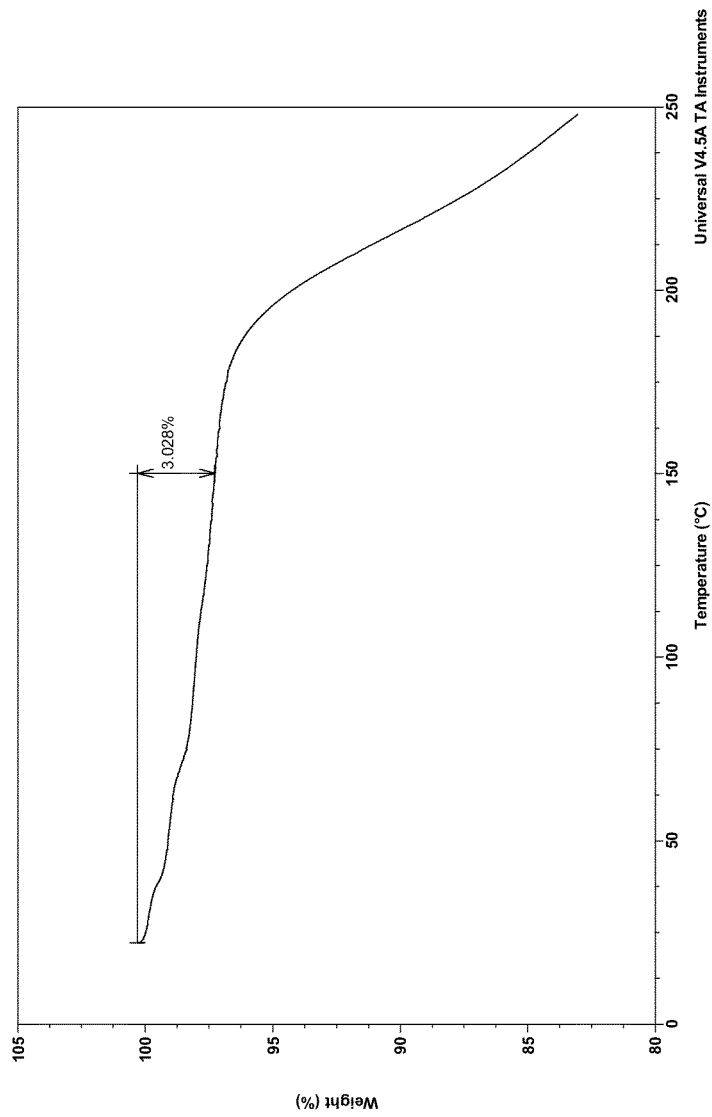
FIG. 25 is a thermogravimetric analysis (TGA) of Compound I Form XI.

In one embodiment, Compound I Form XI is characterized by a weight loss, as measured by thermogravimetric analysis (TGA), of about 3% at about 160° C. In one embodiment, the TGA is substantially as shown in FIG. 25.

Figure 26:
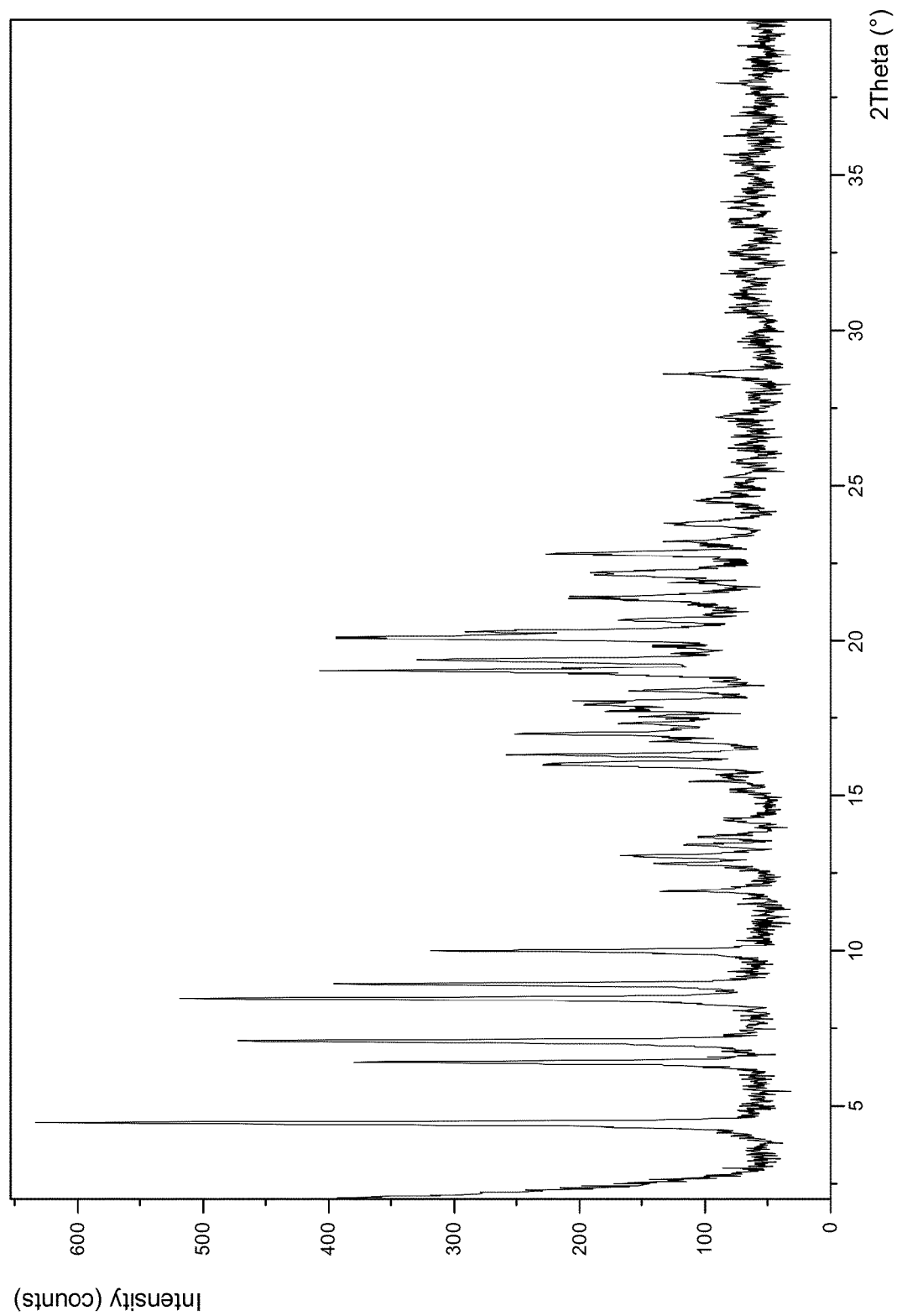
FIG. 26 is an X-ray powder diffraction pattern of Compound I Form XII.

Another embodiment is crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid ethanol solvate (Compound I Form XII), characterized by an X-ray powder diffractogram comprising at least three of the following peaks: 4.5, 6.4, 7.1, 8.5, or 8.9 °2θ±0.2 °2θ, as determined on a diffractometer using Cu-Kα. In one embodiment, the diffractogram comprises peaks at 4.5, 6.4, 7.1, 8.5, and 8.9 °2θ±0.2 °2θ. In one embodiment, the diffractogram is substantially as shown in FIG. 26.

Figure 27:
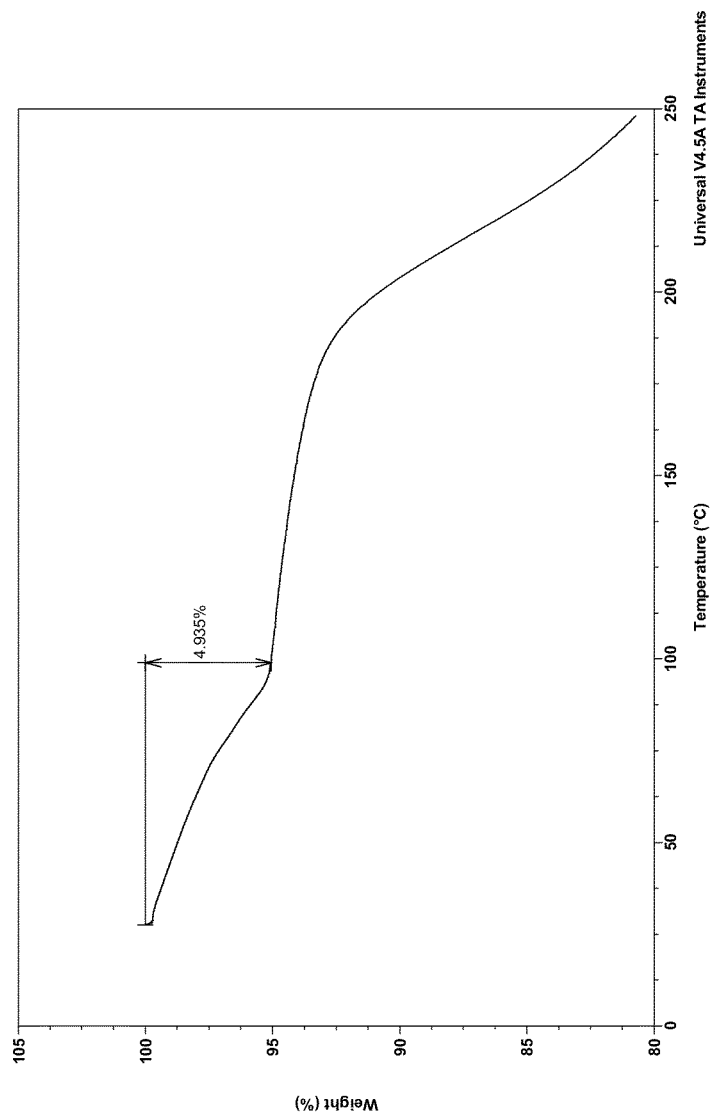
FIG. 27 is a thermogravimetric analysis (TGA) of Compound I Form XII.

In one embodiment, Compound I Form XII is characterized by a weight loss, as measured by thermogravimetric analysis (TGA), of about 4.9% at about 100° C. In one embodiment, the TGA is substantially as shown in FIG. 27.

Figure 28:
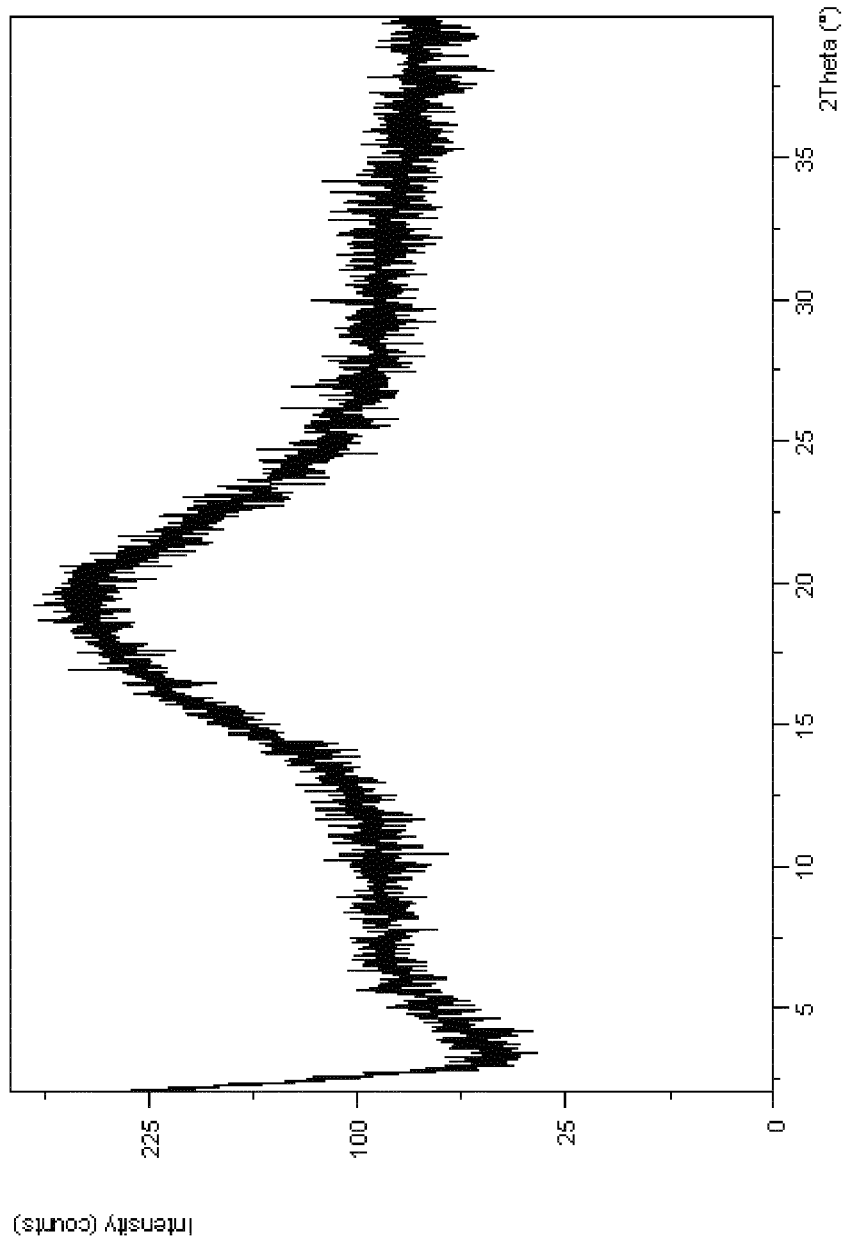
FIG. 28 is an X-ray powder diffraction pattern of amorphous Compound I.

Another embodiment is amorphous 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid isopropyl alcohol solvate (amorphous Compound I). In one embodiment, wherein the X-ray powder diffractogram as determined on a diffractometer using Cu-Kα, diffractogram is substantially as shown in FIG. 28.

Methods of Making Solid Forms of Compound I

One embodiment is a process for making Compound I Form I comprising contacting a 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with water and a solvent selected from the group consisting of acetonitrile, methanol, and acetone, whereby Compound I Form I is formed.

In one embodiment, the method further comprises isolating Compound I Form I.

One embodiment is a process for making Compound I Form II, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with acetonitrile, whereby Compound I Form II is formed.

In one embodiment, the method further comprises isolating Compound I Form II.

One embodiment is a process for making Compound I Form III, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form III is formed.

In one embodiment, the method further comprises isolating Compound I Form III.

One embodiment is a process for making Compound I Form IV, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form IV is formed.

In one embodiment, the method further comprises isolating Compound I Form IV.

One embodiment is a process for making Compound I Form V-MTBE, Compound I Form V-IPA, Compound I Form V-EtOH, Compound I Form V-MEK, or Compound I Form V-2-Me-THF, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with a solvent or solvent mixture selected from the group consisting of methyl tert-butyl ether, isopropyl alcohol and water mixture, ethanol and water mixture, methyl ethyl ketone and heptane mixture, and 2-methyl tetrahydrofuran and heptane mixture, whereby Compound I Form V-MTBE, Compound I Form V-IPA, Compound I Form V-EtOH, Compound I Form V-MEK, or Compound I Form V-2-Me-THF, respectively, is formed.

In one embodiment, the method further comprises isolating Compound I Form V-MTBE, Compound I Form V-IPA, Compound I Form V-EtOH, Compound I Form V-MEK, or Compound I Form V-2-Me-THF.

One embodiment is a process for making Compound I Form VI, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with diisopropyl ether, whereby Compound I Form VI is formed.

In one embodiment, the method further comprises isolating Compound I Form VI.

One embodiment is a process for making Compound I Form VII, comprising contacting 5-(3,3-dimethylbutyn-1-yl)-3-[(cis-4-hydroxy-4-{[(3S)-tetrahydrofuran-3-yloxy]

methyl}cyclohexyl){[(1R)-4-methylcyclohex-3-en-1-yl]carbonyl}amino]thiophene-2-carboxylic acid with isopropyl alcohol, whereby Compound I Form VII is formed.

In one embodiment, the method further comprises isolating Compound I Form VII.

One embodiment is a process for making Compound I Form VIII, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol and water, whereby Compound I Form VIII is formed.

In one embodiment, the method further comprises isolating Compound I Form VIII.

One embodiment is a process for making Compound I Form IX, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with ethanol, whereby Compound I Form IX is formed.

In one embodiment, the method further comprises isolating Compound I Form IX.

One embodiment is a process for making Compound I Form X, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with methyl ethyl ketone, whereby Compound I Form X is formed.

In one embodiment, the method further comprises isolating Compound I Form X.

One embodiment is a process for making Compound I Form XI, comprising desolvating Compound I Form X, whereby Compound I Form XI is formed.

In one embodiment, the method further comprises isolating Compound I Form XI.

One embodiment is a process for making Compound I Form XII, comprising contacting Compound I Form I with ethanol in water, whereby Compound I Form XII is formed.

In one embodiment, the process further comprises isolating Compound I Form XII.

One embodiment is a process for making amorphous Compound I, comprising contacting Compound I Form II with dichloromethane, whereby amorphous Compound I is formed.

In one embodiment, the process further comprises isolating amorphous Compound I.

Pharmaceutical Compositions

The solid forms of Compound I provided in accordance with the present disclosure are usually administered in the form of pharmaceutical compositions. This disclosure therefore provides pharmaceutical compositions that contain, as the active ingredient, one or more of the solid forms of Compound I described or a pharmaceutically acceptable salt or ester thereof and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents (as indicated in the Combination Therapy section below). Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously orally, topically, as an inhalant or via an impregnated or coated device such as a stent, for example or an artery-inserted cylindrical polymer.

One mode for administration is parenteral, particularly by injection. The forms in which the novel compositions of the present disclosure may be incorporated for administration by injection include aqueous or oil suspensions or emulsions, with sesame oil, corn oil, cottonseed oil or peanut oil, as well as elixirs, mannitol, dextrose or a sterile aqueous solution and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the general methods of preparation are vacuum-drying and freeze-drying techniques which yield a powder of the active ingredient plus any additional desired ingredient from a previously sterile-filtered solution thereof.

Oral administration is another route for administration of compounds in accordance with the disclosure. Administration may be via capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include: lubricating agents such as talc, magnesium stearate and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile or on demand delivery of pharmaceutical agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from 1 mg to 2 g of a compound described herein and for parenteral administration, in some embodiments, from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation include solutions and suspensions in pharmaceutically acceptable, aqueous or organic solvents or mixtures thereof and powders. The liquid or solid compositions may contain suitable pharmaceutically acceptable excipients as described supra. In some embodiments, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent or intermittent positive pressure breathing machine. Solution, suspension or powder compositions may be administered, in some embodiments orally or nasally, from devices that deliver the formulation in an appropriate manner.

In one embodiment, this disclosure relates to a pharmaceutical composition comprising a pharmaceutically acceptable excipient or carrier and a therapeutically effective amount of the compound of Formula I as described above or a pharmaceutically acceptable salt, ester, prodrug, stereoisomer or hydrate thereof.

Methods of Use

The solid forms of Compound I described herein are administered to a subject suffering from hepatitis C virus (HCV) in either single or multiple doses by any of the accepted modes of administration known to those who are skilled in the art and as detailed above.

Combination Therapy

Subjects being treated by administration of Compound I forms described in the present disclosure can benefit from treatment with additional therapeutic agents that are effective in treating HCV, or enhance the anti-HCV therapeutic effect of Compound I forms, in accordance with some embodiments. Additional therapeutic agents that are useful for this purpose include, but are not limited to, ribavirin,

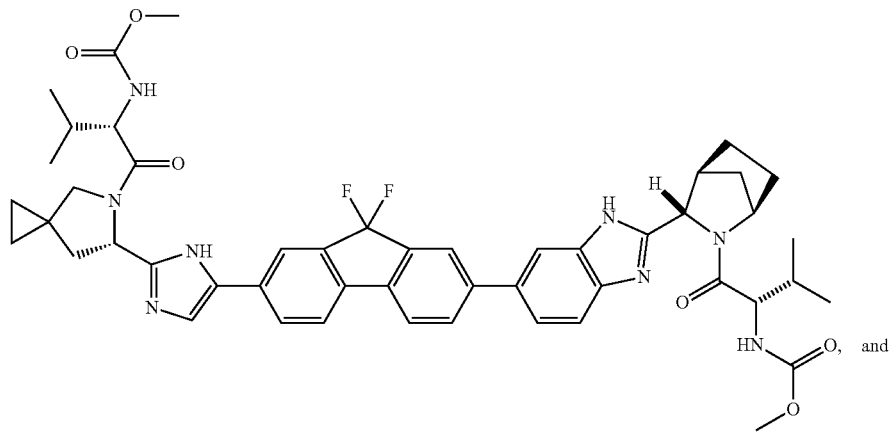

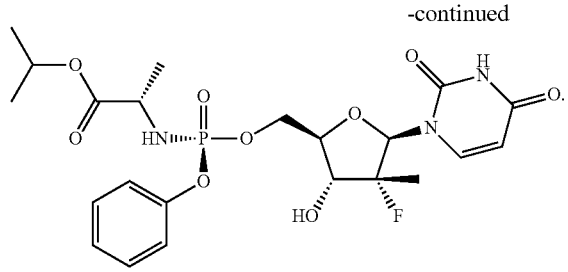

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

EXAMPLES

Example 1

Method of Making 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid

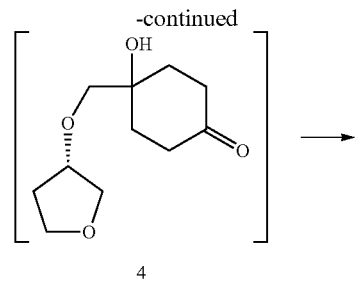

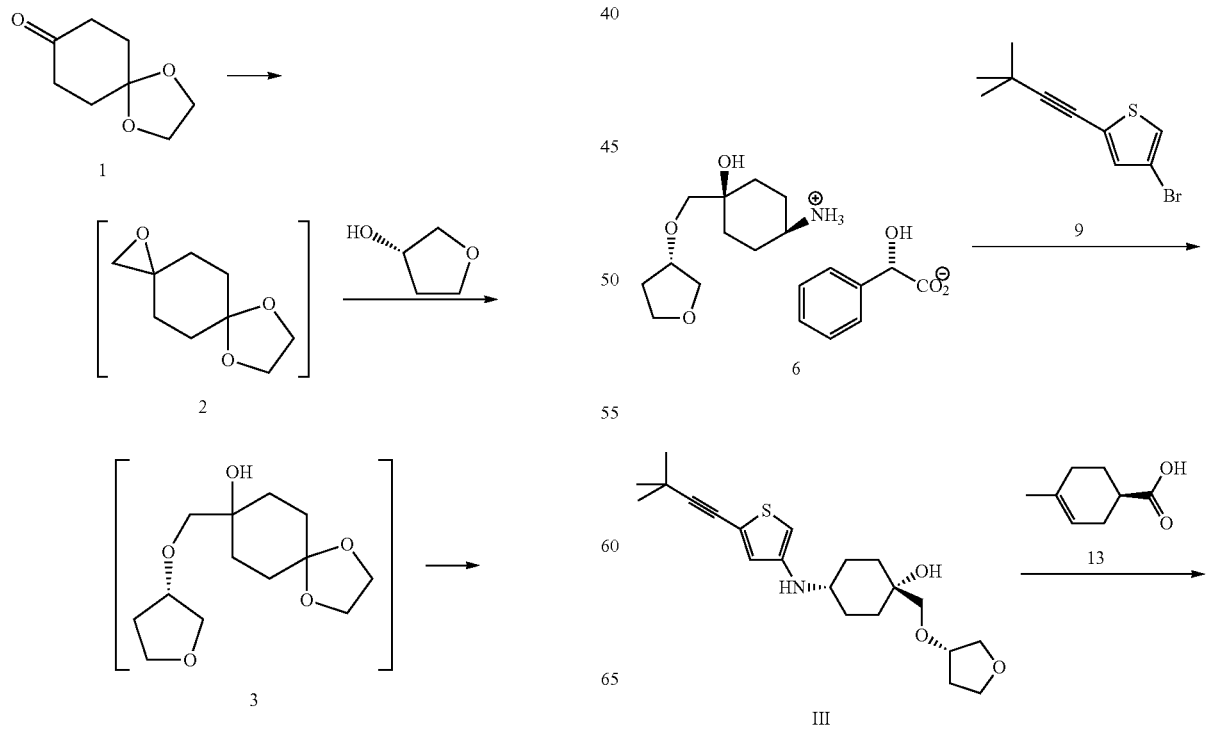

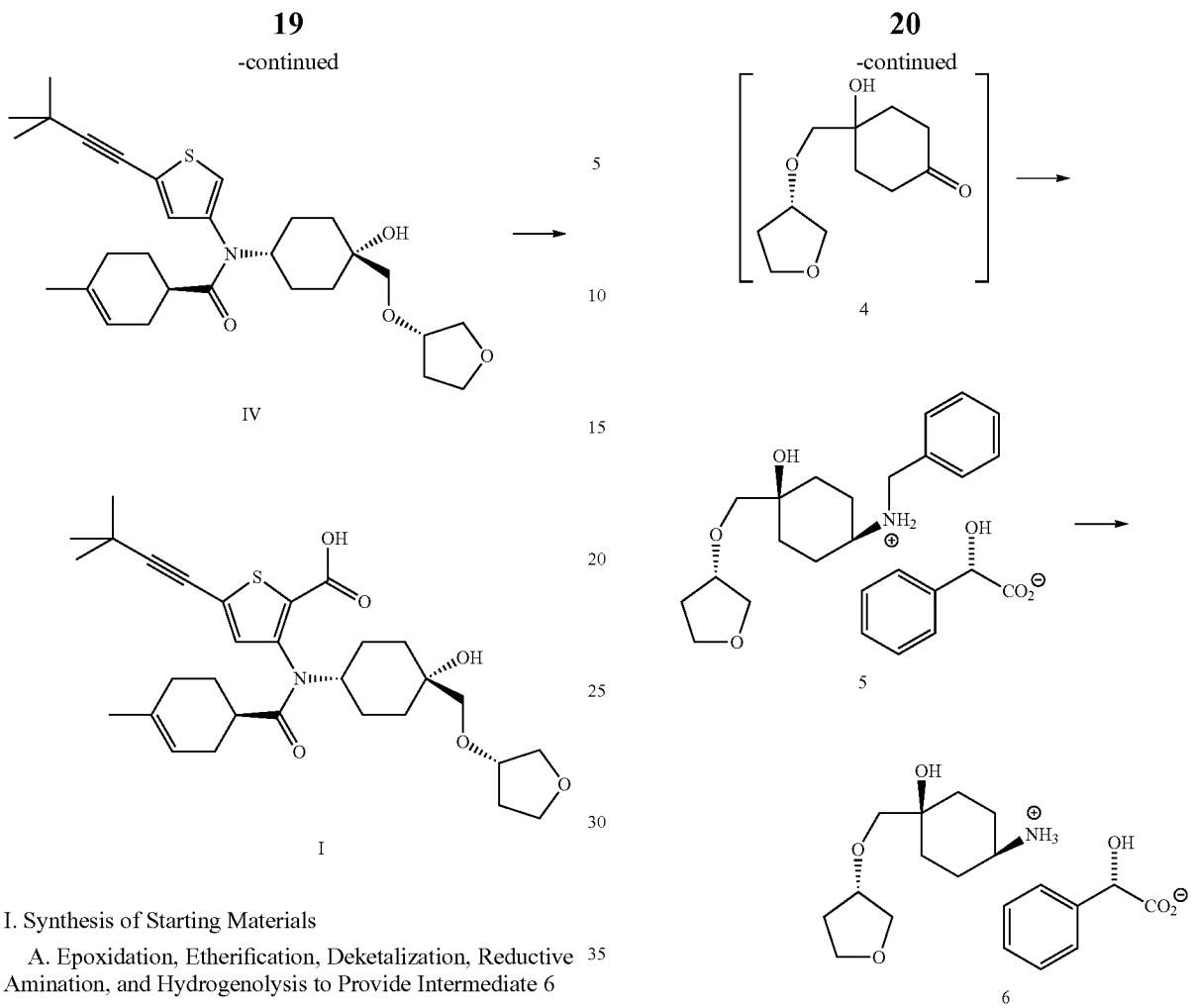

I. Synthesis of Starting Materials

A. Epoxidation, Etherification, Deketalization, Reductive Amination, and Hydrogenolysis to Provide Intermediate 6

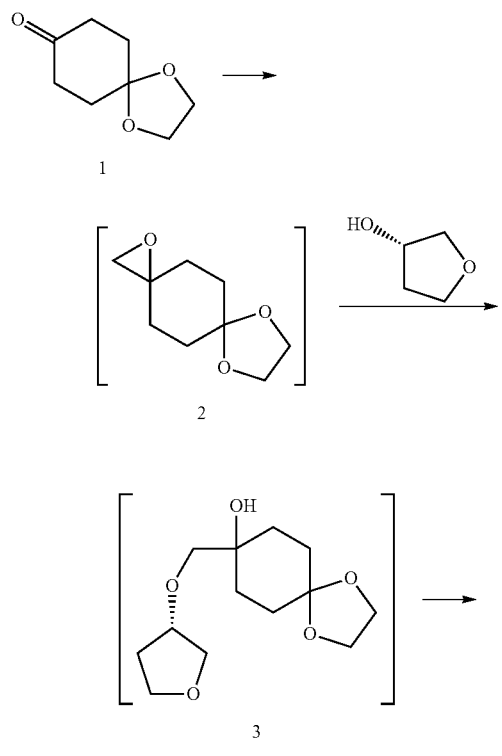

1. Epoxidation to Prepare Intermediate 2

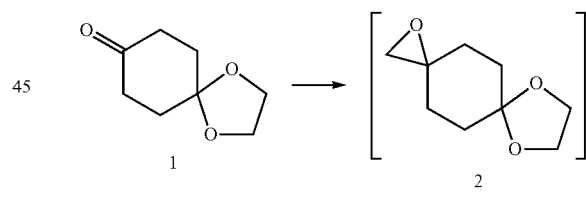

Charge lithium tert-butoxide (1.14 kg, 1.1 equiv) and trimethylsulfoxonium iodide (3.12 kg, 1.1 equiv) to an inerted 70 L reactor with the jacket temperature set to 23° C. Charge DMSO (13.8 kg) and vigorously mix contents between 20 and 25° C. for one hour. Charge 1,4-cyclohexanedione monoethylene acetal (2.02 kg, 1.0 equiv) to the reactor. Once reaction is complete, charge the reactor with brine (18 L, 15 wt %) at a rate to ensure the reaction temperature does not exceed 40° C. Extract the homogenous brine containing reaction mixture with MTBE (3×30 kg) and combine the product containing organics. Concentrate the combined organics by distillation at ambient pressure. Distill off the MTBE to 5 volumes (10 L) to provide a solution of 2 in MTBE.

$^1$H NMR (400 MHz, CDCl$_3$) δ 4.02-3.91 (m, 4H), 2.67 (s, 2H), 1.95-1.83 (m, 4H), 1.81-1.72 (m, 2H), 1.60-1.53 (m, 2H).

2. Etherification to Prepare Intermediate 3

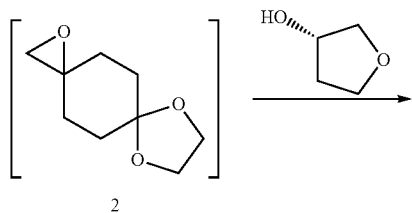

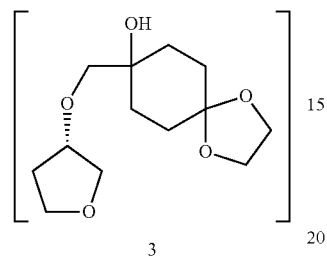

Charge the solution of 2 in MTBE, (S)-tetrahydrofuran-3-ol (1.25 kg, 1.1 equiv), and potassium tert-butoxide (1.59 kg, 1.1 equiv) to an inerted 70 L reactor and heat contents to 55 to 60° C. Upon reaction completion, cool the reactor contents to ambient to afford a solution of 3 in MTBE.

$^1$H NMR (400 MHz, CDCl$_3$) δ 4.19-4.09 (m, 1H), 4.00-3.66 (m, 8H), 3.27 (dd, J=20.1, 8.8 Hz, 2H), 2.04-1.84 (m, 6H), 1.76-1.68 (m, 2H), 1.67-1.50 (m, 2H).

3. Deketalization to Prepare Intermediate 4

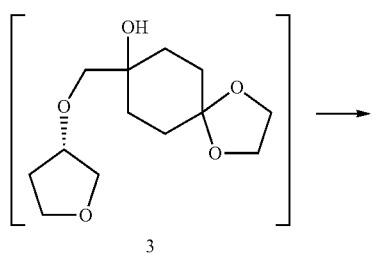

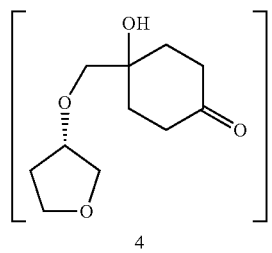

Charge HCl (13.3 L, 1.5 N) to the reactor containing a solution of 3 in MTBE (2.4 kg, 11.1 mmol). Mix the biphasic reaction mixture between 18 and 25° C. Once the reaction is complete, stop agitation and separate the two phases. Extract the aqueous phase with CH$_2$Cl$_2$ (2×L). Combine organic phases in the reactor. Charge aqueous NaHCO$_3$ (15 L, 7.5 wt %) and mix for 1 hour, let settle and split phases. Return organic phase to reactor. Concentrate organics to 5 vol (10 L). Charge 12 L of ethanol and concentrate to 8.5 L to afford 4 as a solution in EtOH. $^1$H NMR (400 MHz, CDCl$_3$) δ 4.17 (m, 1H), 3.95-3.75 (m, 4H), 3.35 (AB, 2H), 2.74 (td, J=13.6, 6.7 Hz, 2H), 2.10-1.97 (m, 5H), 1.71 (td, J=13.6, 6.7 Hz, 2H).

4. Reductive Amination to Prepare Intermediate 5

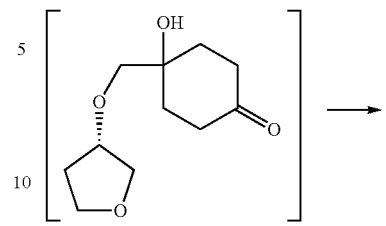

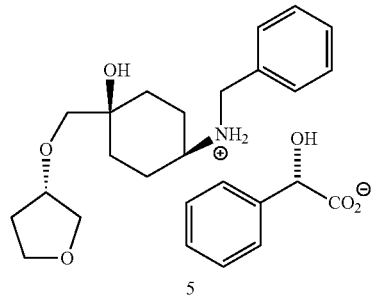

Charge the EtOH solution of 4 to the 70 L reactor (7.84 kg, 30.3 wt %, by $^1$H-NMR), and set the jacket temperature to 20° C. Charge Ti(OiPr)$_4$ (4.0 kg, 1.25 equiv) at a pace to keep the reaction temperature below 30° C. Charge benzylamine (1.2 kg, 1.0 equiv) at a rate to keep the reaction temperature below 35° C. Agitate the reaction mixture for 1 hour at 20° C., then cool the reaction mixture to −4° C. Dissolve sodium borohydride (210 g, 0.5 equiv) in EtOH (5.8 L), and charge to the reaction mixture at a rate to maintain a reaction temperature of not more than 0° C. After 1 hour, add 20 wt % trisodium citrate solution (38 L) and 4-methylpentan-2-one (MIBK, 19.2 L) and set the jacket temperature to 20° C. Agitate the mixture vigorously for 30 minutes, and settle layers. Discard the aqueous layer, and wash the organic phase with 15 wt % NaCl (19 L). Concentrate the organic phase under reduced pressure to an oil. Charge MIBK (7.1 L, 3 vol) and polish filter the turbid solution through a 0.6 micron filter. Transfer the filtrate to the 70 L reactor and charge (S)-mandelic acid (1.7 kg, 1.0 equiv) followed by a small amount of seed crystal. Age the slurry for at least 1 hour, and then add MTBE (9.6 L, 4 vol) over 15 minutes. Filter the slurry and wash the cake with 8.7 L 2/1 MIBK/MTBE. Dry the solid in vacuum oven to afford 5 as white solid.

$^1$HNMR (400 MHz, CD$_3$OD) δ 7.60-7.38 (m, 7H), 7.32-7.18 (m, 3H), 4.21-4.09 (m, 3H), 3.89-3.71 (m, 4H), 3.34-3.19 (m, 2H), 3.12-2.97 (m, 1H), 2.34 (d, J=7.1 Hz, 1H), 1.96 (ddd, J=46.9, 24.1, 3.7 Hz, 2H), 1.85-1.65 (m, 4H), 1.51 (td, J=13.7, 3.7 Hz, 2H).

5. Hydrogenolysis to Prepare Intermediate 6

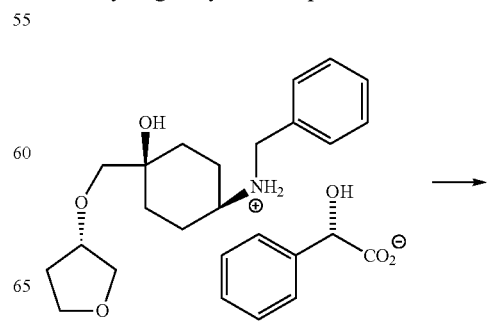

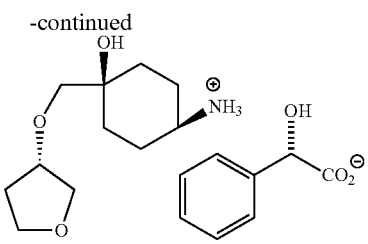

Charge 5 (2.20 kg, 1 equiv) and Pd(OH)$_2$/C (0.12 kg, 20 wt % dry basis, 0.02 equiv) to a 70 L reactor. Inert the reactor and charge MeOH (25.8 L, 10 vol) and ammonium formate (1.52 kg, 5.0 equiv). Warm the reactor contents to 48-50° C. under positive nitrogen pressure and agitate. When the reaction is complete, cool the reaction mixture to 18 to 25° C., and filter the reaction mixture to remove the solids. Solvent exchange through distillation under reduced pressure to isopropanol (IPA) targeting a final volume of 12 L (5 vol). Filter the slurry and wash the cake with IPA (4 L, 2 vol). Dry the solid in vacuum oven at 40° C. to obtain 6 as white solid.

$^1$H NMR (400 MHz, CD$_3$OD) δ 7.50-7.42 (m, 2H), 7.33-7.15 (m, 3H), 4.15-4.06 (m, 1H), 3.92-3.59 (m, 4H), 3.37-3.13 (m, 4H), 2.94 (td, J=10.7, 5.6 Hz, 1H), 1.97 (td, J=7.7, 4.4 Hz, 2H), 1.87-1.59 (m, 7H), 1.55-1.39 (m, 2H).

B. Bromination, De-Bromination, and Alkynylation to Provide Intermediate 9

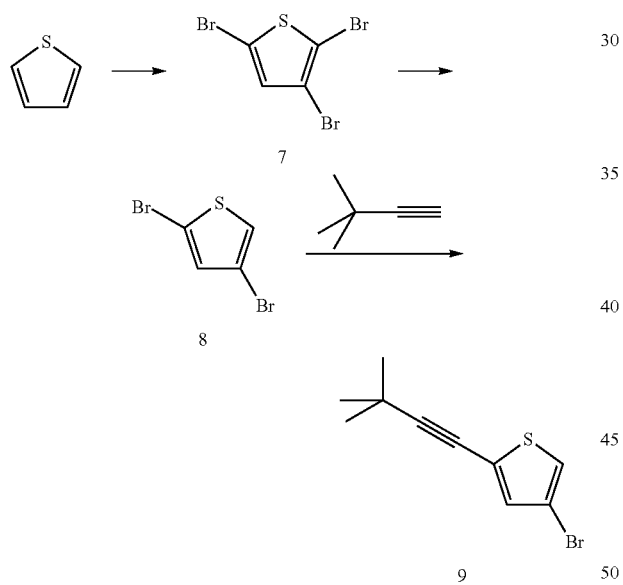

1. Bromination to Prepare Intermediate 7

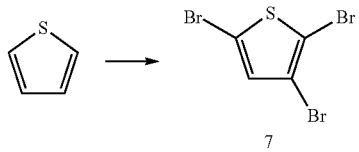 [SMILES: c1ccsc1 ; Brc1cc(Br)c(Br)s1]

A reactor was charged with a solution of aqueous hydrobromic acid (47.6%, 125.0 kg, 5 equiv). Thiophene (12.5 kg, purity 99%, 1 equiv) was added to it at 25-30° C. Tetrabutylammonium bromide (0.625 kg, 0.13 equiv) was added to the reaction mass. The reaction mass was heated to 50-55° C. 50% Aqueous hydrogen peroxide solution (31.3 kg, 3.1 equiv) was added to the reaction mass over 10 h keeping the temperature in the range of 50-55° C. The reaction mass was then heated to 70-75° C. After reaction completion, the reaction mass was cooled to 20-25° C. and washed with 20% sodium metabisulphite solution (17 L), 2 N sodium hydroxide solution (62 L) and the crude product was subjected to fractional distillation using a 2 ft wire-mesh packed column to afford 2,3,5-tribromothiophene. The spectral properties of this molecule are consistent with commercially available material.

2. De-Bromination to Prepare Intermediate 8

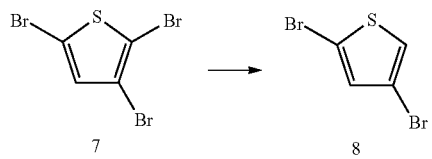 [SMILES: Brc1cc(Br)c(Br)s1 ; Brc1csc(Br)c1]

Dimethyl sulfoxide (DMSO, 330 L) was charged to reactor. 2,3,5-tribromothiophene (33 kg, 1.0 equiv) was charged to the reaction mass under stirring. The reaction mass was cooled to 15-20° C. Sodium borohydride (7.8 kg, 2.0 equiv) was charged lot wise to the reaction mass in 2.0 h maintaining temperature 15 to 20° C. The reaction mass was heated to 20 to 25° C. and maintained until the reaction was completed. The reaction mass was quenched in water (660 L) at 10 to 15° C. and the product was extracted into toluene (5×165 L). The combined organic layer was washed with water (165 L). The organic layer was dried over anhydrous sodium sulfate (8.0 kg) and concentrated under reduced pressure below 50° C. to yield 2,4 dibromothiophene. The spectral properties of this molecule are consistent with commercially available material.

3. Alkynylation to Provide Intermediate 9

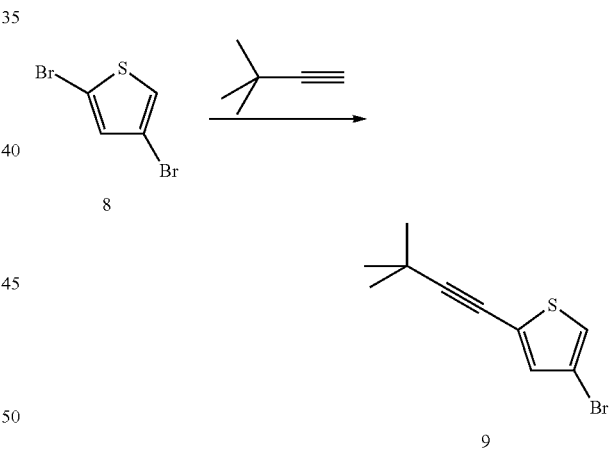

A reactor was evacuated and flushed with nitrogen. Dimethyl formamide (560 L) and 2,4-dibromothiophene (37.5 kg, 1.0 equiv) were charged to the reactor. The reaction mass was cooled to 20-25° C. Palladium chloride bis-triphenylphosphine complex (3 kg, 0.03 equiv) was charged to the reaction mass followed cuprous iodide (1.6 kg, 0.06 equiv), t-butyl acetylene (13.0 kg, 1.1 equiv) and triethylamine (43 kg, 3.0 equiv). The reactor was again flushed with nitrogen and pressurized with 0.50 kg nitrogen (extra pure) pressure. The reaction mass was heated to 25-30° C. and agitated until reaction completion (ca. 6 h). The reaction mass was filtered and the filter cake was washed with dimethyl formamide (37.5 L). The filtrate was concentrated under reduced pressure at a temperature below 50° C. The residue was dissolved in heptane (187.5 L) at 25 to 30° C. The solids were filtered off and washed with heptane (3×56 L). The filtrate was washed successively with 5% ammonia solution and saturated NaCl solution. The organic layer was further dried over anhydrous sodium sulfate and concentrated under vacuum at a temperature below 70° C. The crude oil was purified by fractional distillation to provide 9.

$^1$H NMR (400 MHz, CDCl$_3$) δ 7.00 (s, 1H), 6.96 (s, 1H), 1.26 (s, 9H).

C. Diels-Alder and Saponification to Provide Intermediate 13

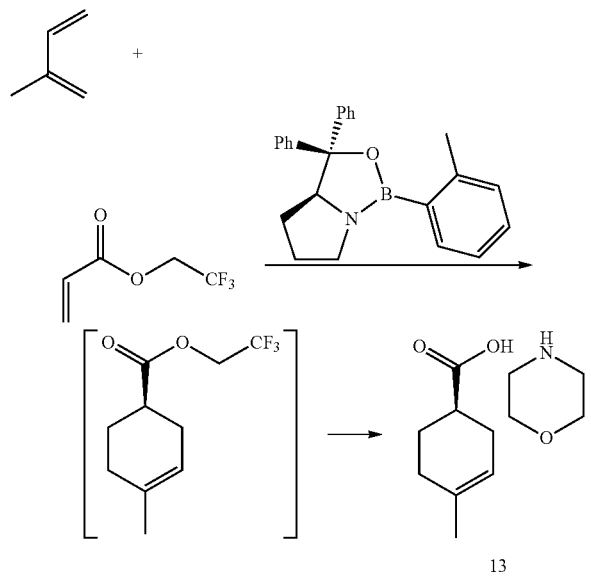

Charge a reactor with (S)-diphenylprolinol (1.26 kg, 0.0625 equiv) and tri-o-tolylboroxine (0.59 kg, 0.0213 equiv) and toluene (40 L). Concentrate the reactor contents at atmospheric pressure until an approximate volume of 10 L. Cool the reaction mixture to 0° C. and charge a solution of triflimide (1.11 kg, 0.05 equiv) in anhydrous DCM (7.3 L) at a rate to ensure the reaction temperature does not exceed 10° C. Charge 2,2,2-trifluoroethyl acrylate (12.2 kg, 1.0 equiv) at a rate to ensure the temperature does not exceed 10° C. Cool the mixture to 0° C. and charge isoprene (8.05 kg, 2.0 equiv) slowly over approximately 4 h maintaining a reaction temperature of 0° C. Upon reaction completion, concentrate the reaction mixture until the content of DCM is less than 20% relative to the intermediate ester. Charge tetrahydrofuran (THF, 69 L) and heat the solution to 40° C. Charge a solution lithium hydroxide monohydrate (LiOH.H$_2$O, 4.0 kg, 1.2 equiv) in 46 L of water over 1 h and stir until the saponification reaction is complete as determined by TLC. Concentrate the reaction mixture until less than 20 mol % THF remains relative to 13 by NMR. Charge methyl tert-butyl ether (MTBE, 50 L) and wash with water (6.1 L). Back extract the aqueous layer with MTBE (2×50 L). Discard the combined organics and concentrate product containing aqueous phase until than 5 mol % MTBE remains relative to 13. To the aqueous mixture charge heptane (46 L) and DCM (2.4 L). Wash the biphasic mixture with 4 M HCl (31 kg). Back extract the aqueous layer with n-heptane (52 L) and wash combined organics with 0.1M HCl (15 kg), and 20% brine (38 kg). To the organic solution of 13 in DCM/heptane charge morpholine (6.9 kg, 1.05 equiv) over 2 h at 20° C. Filter the resulting slurry and wash the filter cake with n-heptane (36 L). Drying the solids under vacuum at 35° C. provides 13 (98.4% ee).

$^1$H NMR (400 MHz, CDCl$_3$) δ 7.76 (s, 2H), 5.39-5.37 (m, 1H), 3.77-3.74 (m, 4H), 2.98-2.96 (m, 4H), 2.48-2.41 (m, 1H), 2.27-2.12 (m, 2H), 2.10-1.90 (m, 3H), 1.74-1.62 (m, 1H), 1.65 (s, 3H).

II. Synthesis of Compound I

A. N-Arylation, acylation, and carboxylation to provide Compound I

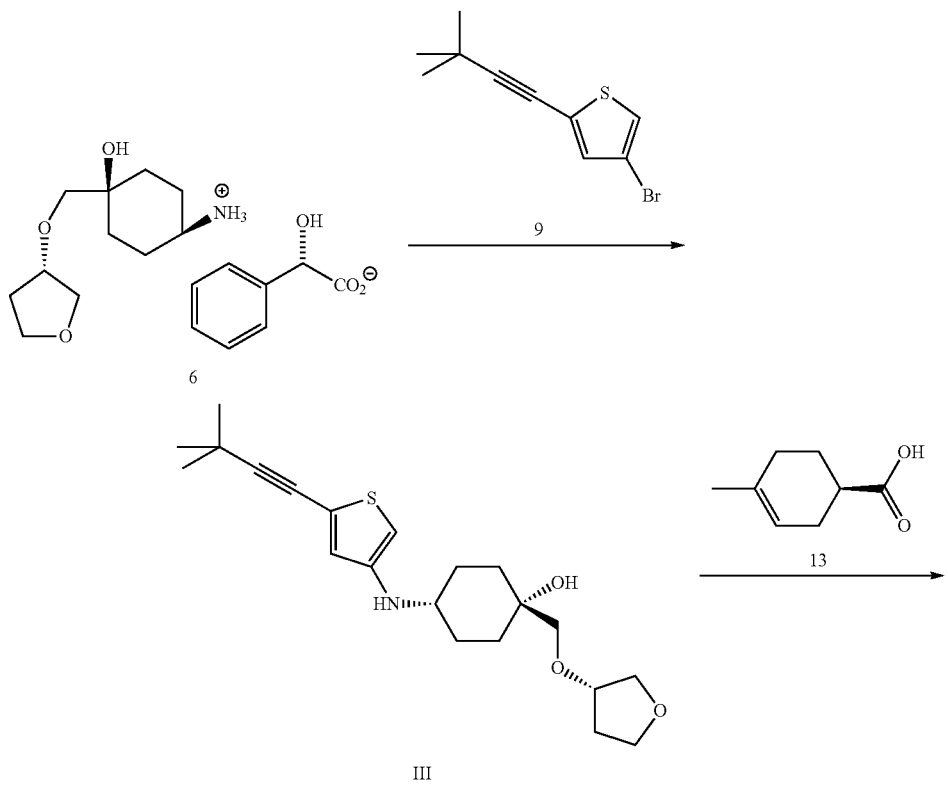

-continued

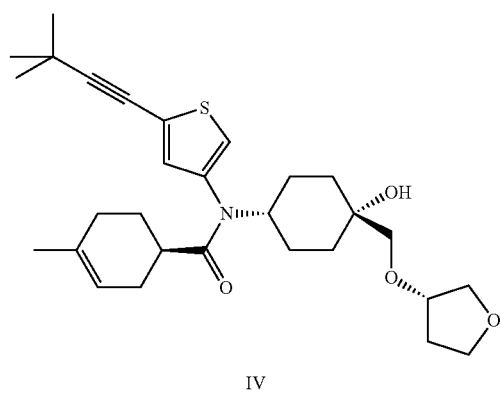

IV

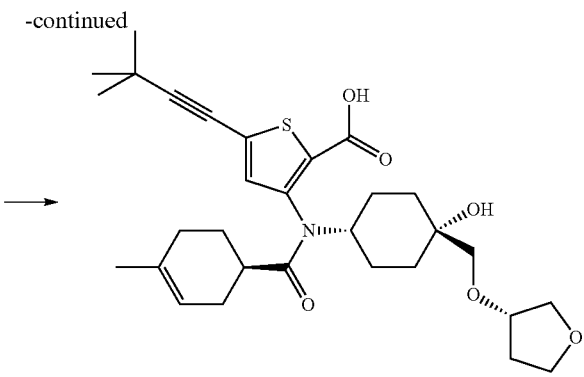

I

1. N-Arylation to Prepare Formula III

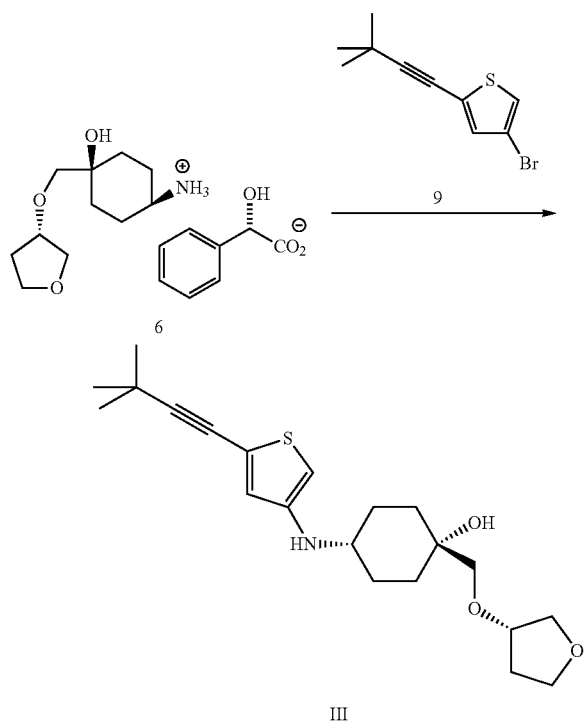

Charge a 125-mL reaction vessel with $Pd_2(dba)_3$ (57 mg, 0.3 mol %), t-Bu-BippyPhos (0.63 g, 7 mol %), and KOH (3.5 g, 3.0 equiv). Inert the vessel and charge t-amylalcohol (40 mL, 8 vol), water (2 mL, 0.4 vol), 6 (9.1 g, 1.2 equiv), and 9 (5.0 g, 1.0 equiv). Inert vessel and heat reactor contents to 90° C. until the reaction is complete as determined by the consumption of 9. Cool reaction mixture to 23° C. and concentrate mixture under reduced pressure to give brown solids. Purify crude solids by silica gel chromatography in EtOAc to provide III as a tan solid having 99.9:0.1 diastereomeric ratio by achiral HPLC.

$^1$H NMR (400 MHz, $CDCl_3$) δ 6.60 (d, J=2.0 Hz, 1H), 5.78 (d, J=2.0 Hz, 1H), 4.16-4.10 (m, 1H), 3.88 (dd, J=16.6, 7.9 Hz, 1H), 3.84-3.76 (m, 3H), 3.25 (dd, J=19.2, 8.7 Hz, 2H), 3.09-2.98 (m, 1H), 2.01-1.95 (m, 2H), 1.94-1.90 (m, 2H), 1.77-1.74 (m, 2H), 1.59-1.44 (m, 2H), 1.42-1.31 (m, 2H), 1.29-1.27 (m, 9H).

2. Acylation to Provide Formula IV

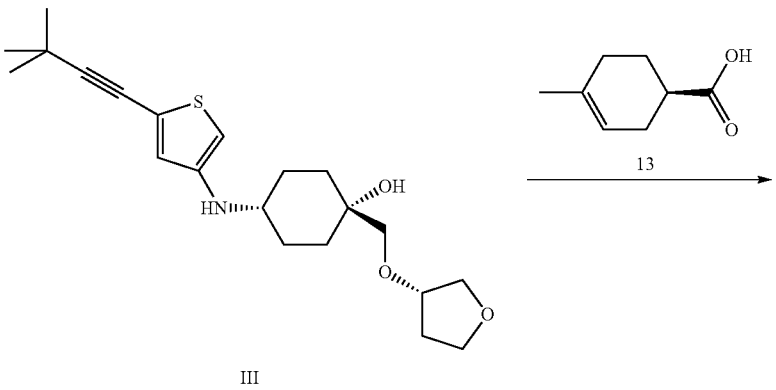

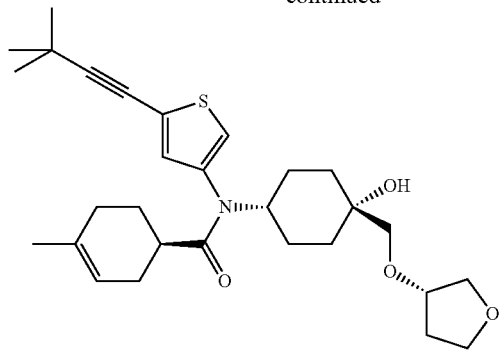

IV

A 15-mL flask equipped with a magnetic stir bar and a nitrogen inlet was charged with 13 (557 mg, 1.5 equiv), 2-methyl-THF (5 mL) and a drop of DMF (ca. 2 μL). The reaction mixture was cooled to 4° C. using an ice bath. To the reaction mixture was added oxalyl chloride (0.32 mL, 1.4 equiv) dropwise over 1 min. The reaction mixture was allowed to warm to 19° C. over 30 min and aged at 19° C. for 3 h. To a 50-mL flask equipped with a magnetic stir bar and a nitrogen inlet were added III (1.00 g, 1.0 equiv), MeTHF (5 mL) and diisopropylethylamine (1.38 mL, 3 equiv), and the contents were cooled to 7° C. using an ice bath. To the slurry of III was added the solution of the acid chloride dropwise over 5 min. The reaction mixture was allowed to warm to 17° C. over 30 min and aged for 3 h. The reaction mixture was quenched with 10 wt % aqueous citric acid (10 mL) and the phases were separated. The organic phase was washed with water (10 mL) and concentrated under reduced pressure. The residue was dissolved in isopropanol (25 mL) and concentrated to ca. 5 mL. To the solution was added water (5 mL) over 10 min and seed crystal of IV (5 mg, 0.5 wt %). The slurry was aged at room temperature for 16 h and filtered. The filter cake was rinsed with 1/1 IPA/water (6 mL) and dried in a vacuum oven for 24 h to afford IV.

$^1$H NMR (400 MHz, CDCl$_3$) δ 6.86 (d, J=1.8 Hz, 1H), 6.82 (d, J=1.8 Hz, 1H), 5.30-5.25 (m, 1H), 4.55-4.45 (m, 1H), 4.15-4.03 (m, 2H), 3.89-3.72 (m, 4H), 3.32-3.20 (m, 2H), 2.30-2.18 (m, 2H), 1.99-1.67 (m, 11H), 1.56-1.36 (m, 4H), 1.34-1.30 (m, 9H).

3. Carboxylation to Provide Compound I

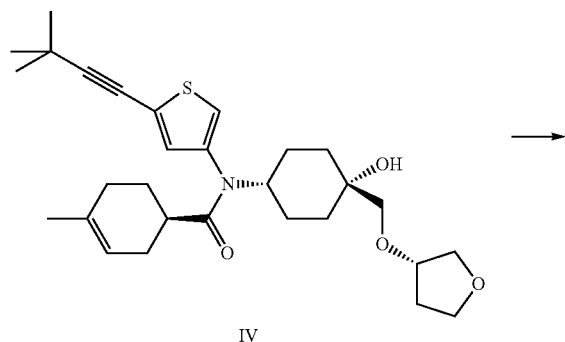

IV

→

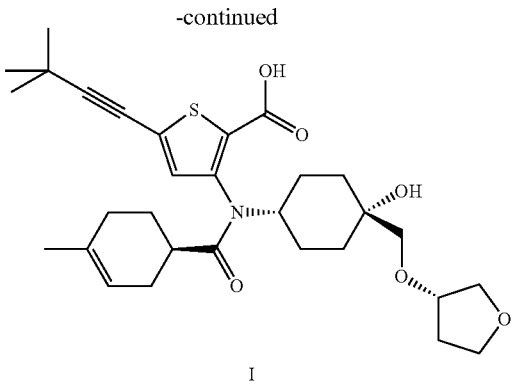

I

In a 50 mL flask, IV (1.00 g, 1.0 equiv) and THF (10 mL) were placed, and the solution was cooled to -11° C. using acetone/ice bath. To the solution was added n-BuLi (2.4 mL, 2.5 M solution in hexanes, 3 equiv) over 10 min maintaining internal temperature below -3° C. The reaction mixture was allowed to age between -12° C. to -10° C. for 1 h. Carbon dioxide (lecture bottle equipped with a pressure regulator) was introduced through a needle, and the bubbling was continued for 10 min. The reaction mixture was aged at -10° C. for 1 h, quenched with 10 wt % aqueous citric acid (10 mL) and allowed to warm to 19° C. The layers were separated and the organic solution was diluted with isopropyl acetate (50 mL). The solution was concentrated to ca. 5 mL under reduced pressure. To the solution was then added benzylamine (0.22 mL, 1 equiv). The slurry was aged for 30 min, and filtered. The filter cake was rinsed with iPAc (10 mL). In a 50 mL flask were added the wet cake of I, iPAc (10 mL) and 10 wt % aqueous citric acid (10 mL). The mixture was stirred until all solids dissolved, and the phases were separated. The organic phase was washed with water (10 mL), and diluted with iPAc (50 mL). To the slurry was added heptane (10 mL) over 2 h, and the slurry was filtered. The filter cake was washed with 2/1 heptane/iPAc (6 mL) and dried in vacuum oven. Note: Slow interconversion between two rotamers on NMR timescale gives rise to two sets of NMR signals.

$^1$H NMR (400 MHz, DMSO-d6) δ 13.48 (br. s., 1H), 7.21, s; 7.16, s, (1H), 5.28, m; 5.24, m, (1H); 4.32 (m, 1H); 4.06 (m, 1H); 3.99 (br. s, 1H); 3.70 (dd, J=8.0, 15.2 Hz, 1H); 3.65 (ddd J=8.0, 15.2, 3.2 Hz, 1H); 3.63 (m, 2H); 3.10 (dd, J=9.6, 1.6 Hz, 1H), 3.06 (d, J=9.6 Hz, 1H), 2.20, m; 2.09, m, (1H); 2.05, m; 1.90, m, (1H); 1.86 (m, 2H); 1.86, m; 1.82, m, (1H); 1.80, m; 1.76, m, (1H); 1.70, m; 1.64, m (1H); 1.68, m; 1.63, m (1H); 1.55, m; 1.38, m (1H); 1.54, m; 1.42, m (2H); 1.52 (s, 3H); 1.48, m; 1.16, m (2H); 1.46 (m, 2H); 1.42 (m, 2H); 1.30, s, 1.29, s (9H).

Example 2

Form Screening

I. Stable Form Screening

A. Initial Stable Form Screening

The first stable form screening was conducted using 19 solvents/mixtures at ambient conditions. The starting material was amorphous. Anti-solvents, either water or heptane, were used to precipitate the solids. The results are summarized in Table 1.

TABLE 1

Results from the first stable form screening for Compound I

| Solvent | Init. Conc. (mg/mL) | 24 h solids | 2-Week solids | Solubility (mg/mL) | Anti-solvent | Solids |
|---|---|---|---|---|---|---|
| Water | 11 | amorphous | amorphous | ND | — | — |
| ACN | 91.6 | II | II | 13 | — | — |
| MeOH | 87.4 | solution | solution | >87.4 | water | I |
| EtOH | 76 | solution | solution | >76 | water | V |
| Acetone | 79.6 | solution | solution | >79.6 | water | I |
| IPA | 95.4 | solution | solution | >95.4 | water | V |
| MEK | 65.6 | solution | solution | >65.6 | heptane | V |
| MIBK | 60.2 | solution | solution | >60.2 | heptane | II |
| MeCl$_2$ | 36 | solution | solution | >36 | heptane | II |
| THF | 53.4 | solution | solution | >53.4 | water + heptane | I |
| 2 Me-THF | 77.4 | solution | solution | >77.4 | heptane | V |
| EtOAc | 49.4 | solution | solution | >49.4 | heptane | II |
| IPAc | 39.6 | solution | solution | >39.6 | heptane | I + II |
| MTBE | >45 | solution | V | 316 | — | — |
| Toluene | 16.2 | solution | solution | >16.2 | heptane | II |
| Heptane | 12.7 | amorphous | amorphous | ND | — | — |
| EtOH/water | 26 | III | IV | 14.5 | — | — |
| ACN/water | 45.8 | I | I | 0.23 | — | — |
| IPA/water | 47.7 | solution | V | 1.78 | — | — |

After 24 h, three crystalline forms were observed in the slurry. Form I is a hydrate form obtained from ACN/water 50:50 mixture. Form II is an anhydrous form obtained from ACN. Form III is a hydrate/solvate form from ethanol/water mixture, and it converts to Form IV upon drying. Solids in water and heptane were amorphous. Other samples remained as solutions.

After 2 weeks, Form V was obtained in MTBE and IPA/water mixture. It appears to be a solvated form. Additionally, Form III converted to Form IV in the slurry. Solids in water and heptane remained amorphous. Other samples remained as solution.

When anti-solvents (water or heptane) were added to the remaining solutions, all solutions crystallized. No new forms appeared based on XRPD.

B. Follow-Up Stable Form Screening

In the follow-up stable form screening experiments, the starting materials were Form II. The solids were stirring in the solvents list below at about 22° C. in 2 ml vials. Results in Table 2 showed that Form II was stable in most tested solvents except for alcohols, water, and MEK.

TABLE 2

Second stable form screening results

| Solvent | 24 h Form | 2-Week Form | Solubility (mg/mL) |
|---|---|---|---|
| Water | II + I (small amt) | I | 0.25 (I) |
| EtOH/water (52/48) | V | V | 8 (V) |
| ACN | II | II | 6 |
| MeOH | solution | solution | >321 |
| EtOH | IX | IX | 283 (IX) |
| Acetone | II | II | 241 |
| IPA | VII | VII | 266 (VII) |
| MEK | X | X | 127 (X) |
| MIBK | II | II | 116 |
| DCM | solution | solution | >274 |
| THF | solution | solution | >346 |
| 2 Me—THF | solution | solution | >334 |
| Ethyl Acetate | II | II | 124 |
| Isopropyl Acetate | II | II | 59 |

TABLE 2-continued

Second stable form screening results

| Solvent | 24 h Form | 2-Week Form | Solubility (mg/mL) |
|---|---|---|---|
| Methyl t-butyl ether | II | II | 108 |
| Toluene | II | II | 40 |
| Heptane | II | II | 0.05 |
| ACN/water (50/50) | II | II | 18 |

C. Stable Form Competition Study

To further verify the stability of Form II, competitive crystallization was conducted by adding Forms I through V into a high concentration solution of amorphous Compound I in ACN. After stirring overnight, Form II was the only detected form. The mother liquor obtained, which was saturated in terms of Form II, was used in another test in which other forms (Forms I, III, IV and V) were added. Those solids all dissolved quickly, again confirming that Form II was more stable in ACN.

II. Hydrate Screening

A. ACN/Water System

ACN does not form solvates with Compound I, so it is appropriate to use ACN and water mixture in this study. The results are shown in Table 3.

TABLE 3

Hydrate screen using ACN/water

| Water content | Water activity | Equivalent RH (%) | Starting Form | Form at 24 h or 90 h | Form at 2 weeks |
|---|---|---|---|---|---|
| 0% | 0 | 0 | II | II (24 h) | II |
| 4.5% | 0.6 | 60 | II | II (24 h) | II |
| 6.6% | 0.7 | 70 | II | II (24 h) | II |
| 10% | 0.779 | 77.9 | II | II (90 h) | II |
| 11.5% | 0.8 | 80 | II | II (24 h) | II |
| 20% | 0.863 | 86.3 | II | II (90 h) | II |
| 30% | 0.896 | 89.6 | II | II (90 h) | VIII |
| 32% | 0.9 | 90 | II | II (24 h) | VIII |
| 40% | 0.914 | 91.4 | II | II (90 h) | VIII |
| 50% | 0.926 | 92.6 | II | II + small amount VIII (90 h) | VIII |
| 60% | 0.936 | 93.6 | II | VIII + small amount II (90 h) | VIII |
| 70% | 0.943 | 94.3 | II | II (90 h) | VIII |
| 80% | 0.949 | 94.9 | II | II (90 h) | II + VIII |
| 80.9% | 0.950 | 95 | II | I + II (24 h) | I |
| 90% | 0.955 | 95.5 | II | II (90 h) | I |
| 100% | 1 | 100 | II | I + II (24 h) | I |

In this study, Form II was shown to be stable in up to 0.863 water activity (or 86.3% RH) at 22° C. In higher water activity conditions, neither Form VIII or Form I is more stable but the conversion rate is generally slow.

B. EtOH/Water System

When the organic component used in the solvent mixture forms solvate with Compound I, potential hydrates may not show up in the slurry screen, as shown in the hydrate screening using ethanol/water mixtures (Table 4). Form IX is a new form found in this study.

TABLE 4

Hydrate screen using ethanol/water

| Water content | Water activity | Starting Form | Form at 90 hours | Form at 2 weeks |
|---|---|---|---|---|
| 0% | 0 | II | IX | IX |
| 10% | 0.510 | II | solution | solution |
| 20% | 0.654 | II | solution | solution |
| 30% | 0.721 | II | V | V |
| 40% | 0.770 | II | V | V |
| 50% | 0.806 | II | III + small amount V | V |
| 60% | 0.838 | II | III | IV |
| 70% | 0.866 | II | III | IV |
| 80% | 0.893 | II | I | I |
| 90% | 0.921 | II | I | I |
| 100% | 1 | II | I | I |

C. Form II Stability in Water at Elevated Temperature

Figure 6:
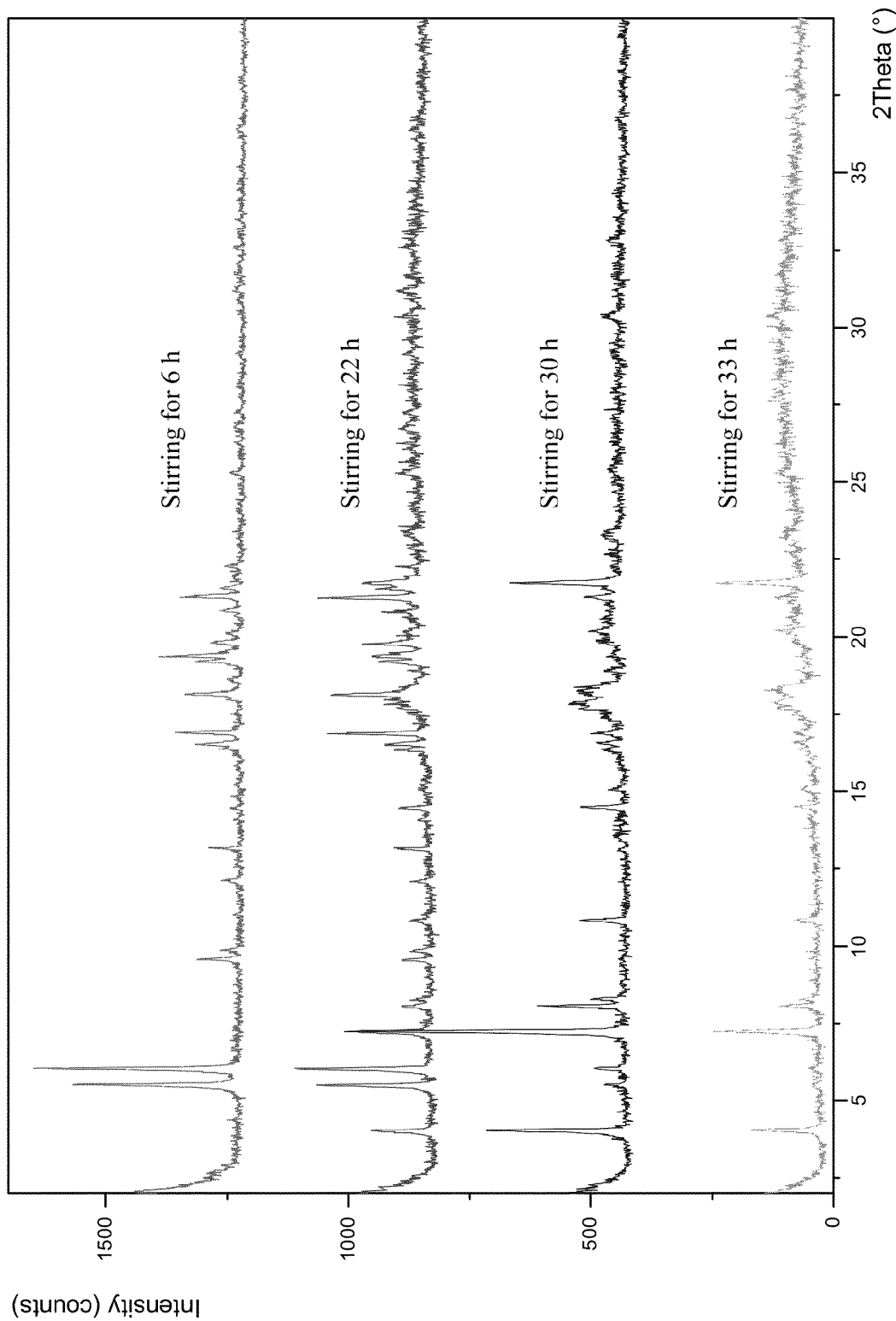
FIG. 6 is an X-ray powder diffraction pattern showing that Form II converts slowly to Form I in water at 48° C.

During formulation, Compound I may be wet granulated and dried at <50° C. A slurry of Form II in water was stirred at 48° C. (50° C. jacket) and was sampled periodically for XRPD analysis to determine Form I content. Based on FIG. 6, Form I was not detected at the 6 hour point; the sample slowly converted to Form I; and after 30 hours, Form I became the dominant form in the XRPD. The XRPD for Form I is as shown in FIG. 1.

III. Desolvation Screening

Another method of generating anhydrous forms is desolvation. In this study, the solvates and hydrates of Compound I were heated to about 110~120° C. in a vacuum oven to desolvate. The results are shown in Table 5.

TABLE 5

Desolvation of different forms

| Form | Solvent | TGA desolvation Temp | Oven Temp | Final Form |
|---|---|---|---|---|
| I | Water | 40-70° C. | 110~120° C. | Amorphous |
| V | EtOH/water (52/48) | 50-140° C. | 110~120° C. | Amorphous |
| VI | DIPE | 100-150° C. | 110~120° C. | VI |
| VII | IPA | 100-130° C. | 110~120° C. | Amorphous |
| VIII | Water/ACN (60:40) | 50-80° C. | 110~120° C. | VIII |
| IX | EtOH | 100-150° C. | 110~120° C. | IX |
| X | MEK | 50-125° C. | 110~120° C. | XI |

In this study, Form X changed to Form XI upon heating.

IV. Summary of the Crystalline Solids of Compound I

Table 6 summarizes the crystalline forms observed in the stable form screenings, hydrate screening, and desolvation screening. Form XII, which was found later, is also included in this table.

TABLE 6

Comparison of the various forms of Compound I

| Forms | Classification | Compatible solvents | Melting point (° C.) | Weight loss by TGA (%) |
|---|---|---|---|---|
| I | hydrate | Water, ACN/water, MeOH/water, acetone/water, THF/water | 123 | 5.4 |
| II | anhydrous | ACN, MIBK, MIBK/heptane, toluene, DCM/heptane, EtOAc, iPrOAc, MTBE | 161.6 | 0.2 |
| III | hydrate/solvate | EtOH/water | 125 | 4.4 |
| IV | hydrate/solvate | EtOH/water | 125 | 2.8 |
| V | solvate | MTBE, IPA/water, EtOH/water, MEK/heptane, 2Me—THF/heptane | 123~131 | 3.5~4.8 |
| VI | solvate | DIPE | 144 | 4.6 |
| VII | solvate | IPA | 115 | 6.9 |
| VIII | hydrate | ACN/water | 119 | 3.1 |
| IX | solvate | EtOH | 146 | 3.2 |
| X | solvate | MEK | 137 | 3.1 |
| XI | anhydrous | (generated by desolvation of Form X) | 140~150 | 3.0 |
| XII | solvate | EtOH/water | Not determined | 4.9 |

Example 3

Characterization of Form II

I. XRPD

The XRPD pattern for this form and the other forms described herein was obtained in the following experimental setting: 45 KV, 45 mA, Kα1=1.5406 Å, scan range 2. 40°, step size 0.0084°, counting time: 8.25 s. The XRPD pattern of Form II is shown in FIG. 4. Its major characteristic peaks are 5.5, 6.0, 9.6, 9.9, 16.9, 18.3, 21.3° 2θ.

The peaks and relative intensities of the peaks in the XRPD for Form II are provided in Table 7 below.

TABLE 7

Relative intensities of peaks for XRPD of Form II

| No. | Position [°2 θ] | Relative Intensity [%] |
|---|---|---|
| 1 | 5.5 | 100 |
| 2 | 6.0 | 62 |
| 3 | 9.6 | 7 |
| 4 | 9.9 | 9 |
| 5 | 12.1 | 5 |
| 6 | 13.1 | 6 |
| 7 | 14.5 | 2 |
| 8 | 16.5 | 8 |
| 9 | 16.9 | 25 |
| 10 | 18.1 | 19 |
| 11 | 19.2 | 9 |
| 12 | 19.4 | 15 |
| 13 | 19.8 | 16 |
| 14 | 20.1 | 6 |
| 15 | 20.8 | 10 |
| 16 | 21.3 | 24 |
| 17 | 21.5 | 5 |
| 18 | 21.9 | 3 |
| 19 | 25.3 | 2 |
| 20 | 26.8 | 2 |
| 21 | 31.2 | 2 |
| 22 | 36.4 | 1 |

II. TGA and DSC

The TGA and DSC data of Form II are plotted in FIG. 5. Form II is anhydrous and lost 0.2% mass when heated to about 120° C. It has a melting point of about 161.6° C., the highest among all forms discovered so far.

Example 4

Preparation of Form II

The procedure of making Form II is as follows:

A solution of 10 g of Compound I and 70 mL of isopropyl acetate is warmed to 40° C. and optionally seeded with 50 mg Form II seed. The resulting thin slurry is agitated for at least 1 h at 40° C. and then 140 mL heptane was added dropwise over 3 h. The slurry was optionally cooled to 0-5° C. over 2 h and continued to stir at least 2 h. The solids were isolated by filtration and the wet cake was rinsed with 20 mL heptane, and then dried in a vacuum oven at 40° C.

Example 5

Preparation and Characterization of Additional Forms

Form I

Figure 3:
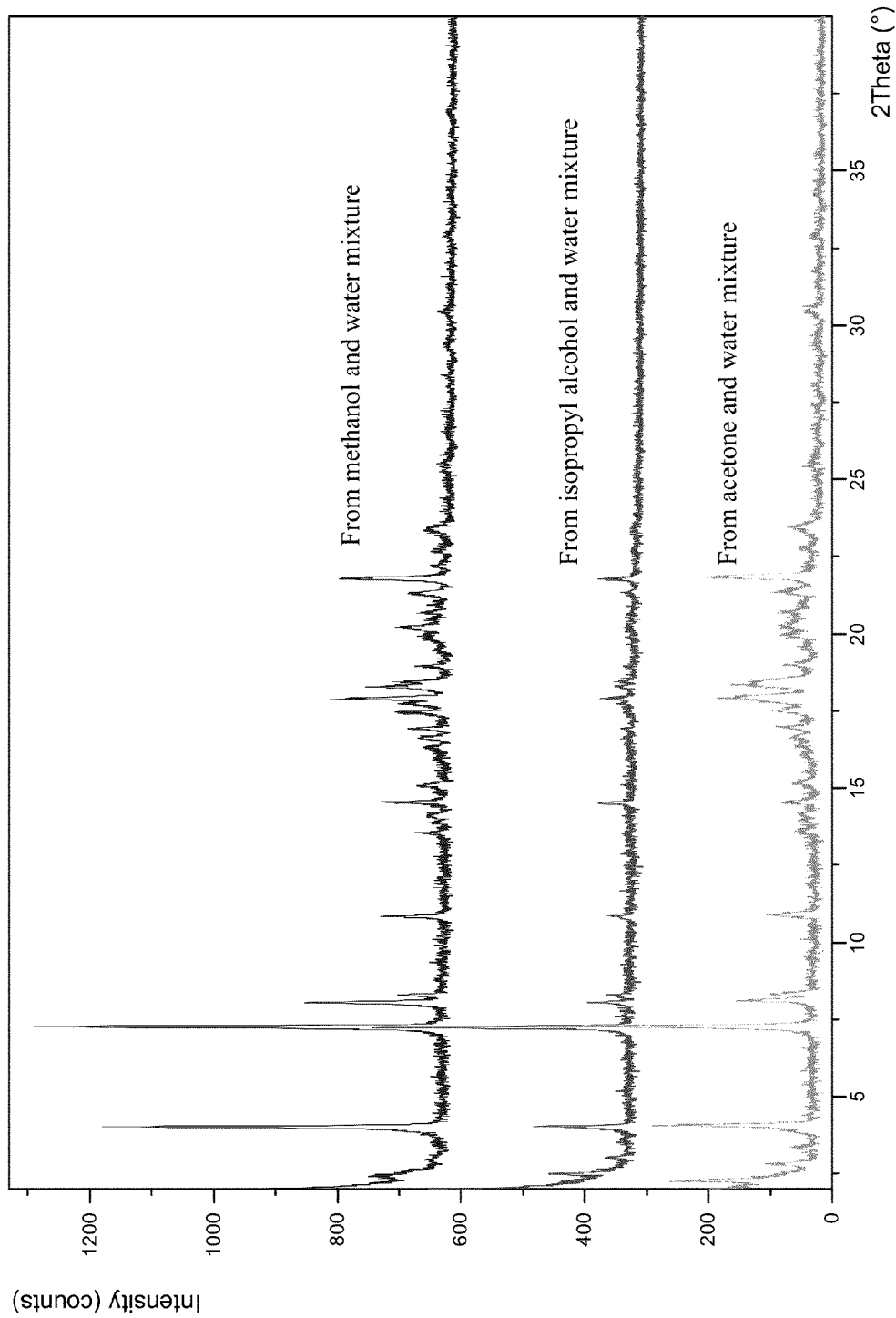
FIG. 3 provides X-ray powder diffraction patterns of Form I obtained from ACN/water, MeOH/water, and acetone/water mixtures.

Form I is a hydrate and was obtained from water and various solvent/water mixtures such as ACN/water, MeOH/water, acetone/water, THF/water. FIG. 3 compares the XRPD patterns of Form I obtained from ACN/water, MeOH/water, acetone/water mixtures. They closely resemble each other.

TGA data are plotted in FIG. 2 of Form I solids. The solids obtained from water (by converting from Form II), ACN/water, MeOH/water, and acetone/water mixtures have similar TGA behavior, and they lost about 5.4% water upon heating. Karl Fischer analysis showed that the solids from ACN/water contain about 5.18% water, which is consistent with the TGA data. The exact stoichiometry of water in the crystal lattice is unknown because 5.4% is between sesquihydrate (4.7%) and lower than dihydrate (6.2%).

Figure 7:
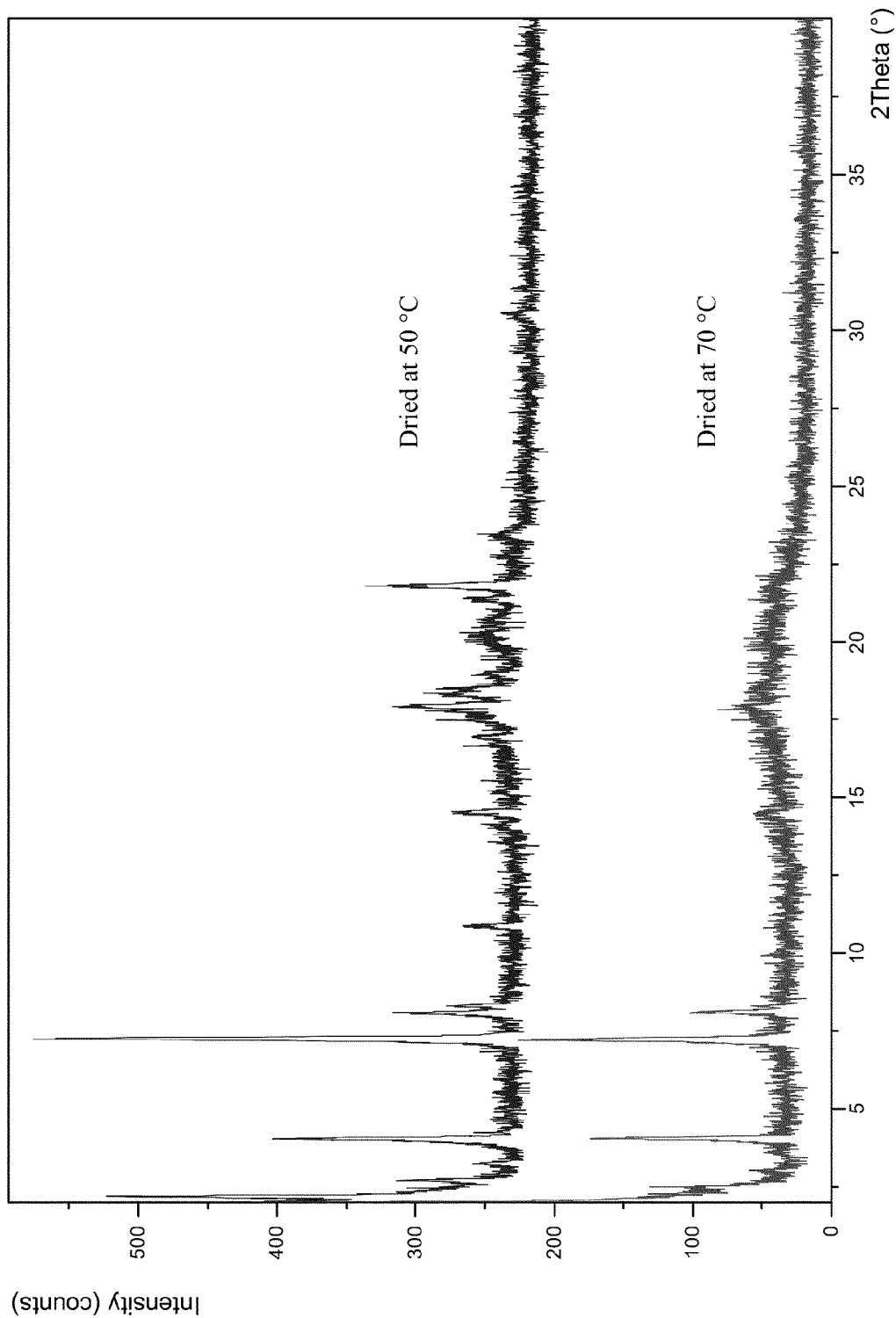
FIG. 7 are X-ray powder diffraction patterns of Form I solids after it was dried at 50° C. and 70° C.

Loss of water during heating caused the crystal lattice to collapse, as confirmed by XRPD patterns at 50 and 70° C. in FIG. 7. The solids partially became amorphous after drying at 70° C.

Forms III and IV

Form III and Form IV emerged in EtOH/water mixture at water contents of 60 to 70% (Table 4). Experiments showed that Form III converted to Form IV upon drying or in slurry after 2 weeks of stirring. Form III (FIG. 8) and Form IV (FIG. 10) have similar XRPD patterns except for shifting of several peaks. TGA data (shown in FIG. 9 and FIG. 11) indicate that they are both hydrate/solvate forms.

Form V

Form V was obtained from MTBE, EtOH/water, IPA/water, MEK/heptane, 2-Me-THF/heptane, and their XRPDs are shown in FIG. 12.

Form V appears to be a solvate form, as shown in FIG. 13 for solids from EtOH/water mixture. The TGA weight losses and melting points are not the same for solids from different solvents, as shown in Table 8. These solids from different solvent systems could be isostructural solvates.

TABLE 8

Comparison of the TGA weight loss and melting temperatures of Form V from different solvents

| | TGA Weight loss (%) | Melting temperature (° C.) |
|---|---|---|
| MTBE | 4.8 | 123.6 |
| IPA/water | 4.2 | Not determined |
| EtOH/water | 3.5 | 130.7 |
| MEK/heptane | Not determined | 124.9 |
| 2Me—THF/heptane | Not determined | 129.1 |

Form VI

Form VI was detected in a sample crystallized from diisopropyl ether (DIPE). The XRPD, TGA and DSC data are shown in FIG. 14 and FIG. 15, respectively. It is a DIPE solvate and lost about 4.7% weight at about 150° C.

In an attempt crystallize Form VI, the solution of Compound I in DIPE was seeded with Form VI. However, only Form II was obtained. This experiment shows that Form II is more stable than Form VI.

Form VII

Form VII appeared in the follow-up stable form screening using IPA as solvent (Table 2). Its XRPD pattern is shown in FIG. 16 and its DSC and TGA data are shown in FIG. 17. This form is a solvate of IPA based on the weight loss of about 6.9% at about 140° C.

Form VIII

Form VIII was obtained in ACN/water system at water contents of 30 to 80% (Table 3). It appears to be a monohydrate according to the weight loss of about 3.1%. The XRPD is shown in FIG. 18 and the DSC and TGA are shown in FIG. 19.

Form IX

Form IX is a solvate of ethanol that appeared in the follow-up stable form screen (Table 2). TGA shows that it is a solvate. The XRPD pattern and TGA data are shown in FIG. 20 and FIG. 21.

Form X

Form X emerged in the follow-up stable form screen (Table 2) using MEK. TGA shows that it is a solvate. The XRPD pattern, TGA and DSC data are shown in FIG. 22 and FIG. 23.

Form XI

Form XI is crystalline solids that formed when Form X (MEK solvate) was heated to about 110~120° C. (Table 5). The XRPD pattern is shown in FIG. 24.

When analyzed by TGA, the sample shows significant weight loss upon heating before reaching about 110° C. (FIG. 25). This was probably caused by absorption of moisture during sample transfer.

Form XII

Form XII was observed in an experiment in which water was adding to Form IX slurries in ethanol in an attempt further precipitate the solute. After stirring overnight, Form XII was the only solids present in the slurry. Its XRD pattern is shown in FIG. 26. It appeared to be a solvate/hydrate as shown by TGA data in FIG. 27.

Amorphous

Amorphous Compound was provided by dissolving 1 g of Form II in 3 mL dichloromethane at ambient temperature. The solution was filtered, and the solvent evaporated at about 30° C. and under vacuum. The solids were further dried in a vacuum oven at 40° C. for 3 h. The XRPD pattern is shown in FIG. 28.

We claim:

1. Crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid hydrate (Compound I Form I) characterized by an X-ray powder diffractogram comprising at least three of the following peaks: 4.0, 7.3, 8.1, 17.9, or 21.8° 2θ±0.2° 2θ, as determined on a diffractometer using Cu-Kα radiation.

2. Compound I Form I of claim 1, wherein the diffractogram comprises peaks at 4.0, 7.3, 8.1, 17.9, and 21.8° 2θ±0.2° 2θ.

3. Compound I Form I of claim 1, wherein the diffractogram is substantially as shown in FIG. 1.

4. Compound I Form I of claim 1, characterized by a differential scanning calorimetry (DSC) curve that comprises two endotherms at about 55° C. to about 115° C. and about 127° C.

5. Compound I Form I of claim 4, wherein the DSC curve is substantially as shown in FIG. 2.

6. Compound I Form I of claim 1, characterized by a weight loss, as measured by thermogravimetric analysis (TGA), of about 5.4% at about 95° C.

7. Compound I Form I of claim 6, wherein the TGA is substantially as shown in FIG. 2.

8. Crystalline 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (Compound I Form II) characterized by an X-ray powder diffractogram comprising at least three of the following peaks: 5.5, 6.0, 16.9, 18.1, or 21.3° 2θ±0.2° 2θ, as determined on a diffractometer using Cu-Kα.

9. Compound I Form II of claim 8, wherein the diffractogram comprises peaks at 5.5, 6.0, 16.9, 18.1, and 21.3° 2θ±0.2° 2θ.

10. Compound I Form II of claim 8, wherein the diffractogram is substantially as shown in FIG. 4.

11. Compound I Form II of claim 8, characterized by a differential scanning calorimetry (DSC) curve that comprises an endotherm at about 162° C.

12. Compound I Form II of claim 11, wherein the DSC curve is substantially as shown in FIG. 5.

13. Compound I Form II of claim 8, characterized by weight loss, as measured by thermogravimetric analysis (TGA), of about 0.2% at about 120° C.

14. Compound I Form II of claim 13, wherein the TGA is substantially as shown in FIG. 5.

15. A method for treating a subject suffering from hepatitis C virus (HCV), comprising administering to the subject a therapeutically effective amount of a compound of claim 1.

16. The method of claim 15, comprising further administering to the subject at least one anti-HCV agent.

17. The method of claim 16, wherein the anti-HCV agent is a compound selected from the group consisting of ribavirin,

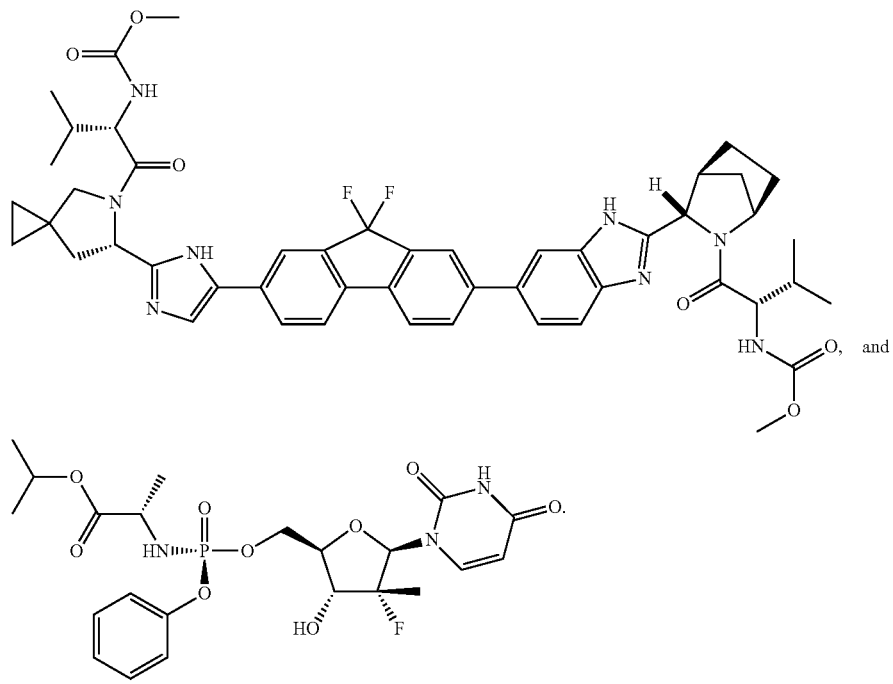

18. A pharmaceutical composition comprising the compound of claim 1 and a pharmaceutically acceptable excipient.

19. A process for making Compound I Form I of claim 1, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with water and a solvent selected from the group consisting of acetonitrile, methanol, and acetone, whereby Compound I Form I is formed.

20. The process of claim 19, further comprising isolating Compound I Form I.

21. A process for making Compound I Form II of claim 8, comprising contacting 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid with acetonitrile, whereby Compound I Form II is formed.

22. The process of claim 21, further comprising isolating Compound I Form II.

23. A method for treating a subject suffering from hepatitis C virus (HCV), comprising administering to the subject a therapeutically effective amount of Compound I Form II of claim 8.

24. The method of claim 23, comprising further administering to the subject at least one anti-HCV agent.

25. The method of claim 24, wherein the anti-HCV agent is a compound selected from the group consisting of ribavirin,

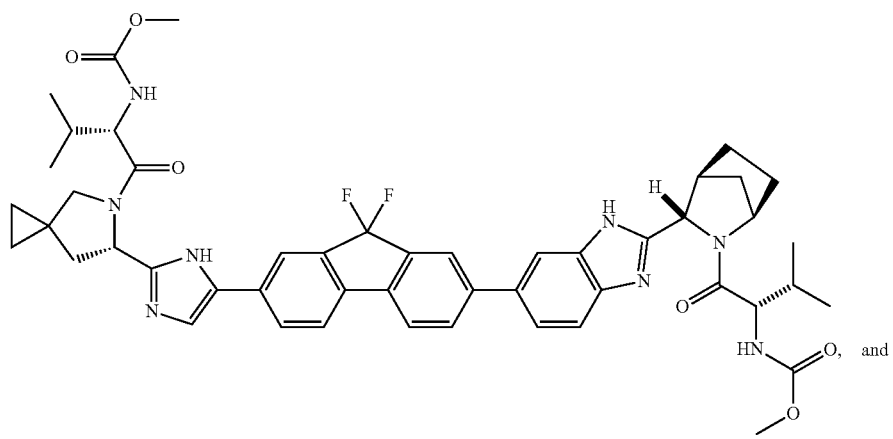

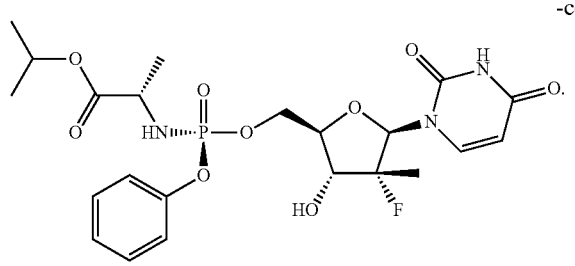
26. A pharmaceutical composition comprising the compound of claim 8 and a pharmaceutically acceptable excipient.
* * * * *